US010080891B2

(12) United States Patent
Thompson-Nauman et al.

(10) Patent No.: US 10,080,891 B2
(45) Date of Patent: Sep. 25, 2018

(54) EXTRA-CARDIOVASCULAR CARDIAC PACING SYSTEM

(71) Applicant: Medtronic, Inc., Minneapolis, MN (US)

(72) Inventors: Amy E. Thompson-Nauman, Ham Lake, MN (US); Melissa G. T. Christie, Ham Lake, MN (US); Mark T. Marshall, Forest Lake, MN (US); Thomas H. Spear, Bloomington, MN (US)

(73) Assignee: Medtronic, Inc., Minneapolis, MN (US)

(*) Notice: Subject to any disclaimer, the term of this patent is extended or adjusted under 35 U.S.C. 154(b) by 139 days.

(21) Appl. No.: 14/957,651

(22) Filed: Dec. 3, 2015

(65) Prior Publication Data
US 2017/0157395 A1 Jun. 8, 2017

(51) Int. Cl.
A61N 1/36 (2006.01)
A61N 1/08 (2006.01)
A61N 1/37 (2006.01)
A61N 1/39 (2006.01)
A61N 1/365 (2006.01)

(52) U.S. Cl.
CPC ........... A61N 1/08 (2013.01); A61N 1/36521 (2013.01); A61N 1/3706 (2013.01); A61N 1/3925 (2013.01); A61N 1/3956 (2013.01)

(58) Field of Classification Search
CPC ............. A61N 1/36521; A61N 1/3706; A61N 1/3943; A61N 1/37; A61N 1/3702; A61N 1/371; A61N 1/3712
See application file for complete search history.

(56) References Cited

U.S. PATENT DOCUMENTS

| 4,343,312 | A  | 8/1982  | Cals et al. |
| 5,387,228 | A  | 2/1995  | Shelton |
| 6,856,835 | B2 | 2/2005  | Bardy et al. |
| 6,952,610 | B2 | 10/2005 | Ostroff et al. |
| 7,082,336 | B2 | 7/2006  | Ransbury et al. |
| 7,092,754 | B2 | 8/2006  | Bardy et al. |
| 7,146,212 | B2 | 12/2006 | Bardy et al. |
| 7,392,081 | B2 | 6/2008  | Wagner et al. |
| 7,502,645 | B2 | 3/2009  | Ostroff et al. |
| 7,734,343 | B2 | 6/2010  | Ransbury et al. |

(Continued)

FOREIGN PATENT DOCUMENTS

| WO | 2004050178 A1 | 6/2004 |
| WO | 2004052444 A2 | 6/2004 |

OTHER PUBLICATIONS (PCT/US2016/059632) PCT Notification of Transmittal of the International Search Report and the Written Opinion of the International Searching Authority, dated Feb. 2, 2017, 11 pages.

(Continued)

Primary Examiner — George Evanisko

(57) ABSTRACT

An extra-cardiovascular medical device is configured to select a capacitor configuration from a capacitor array and deliver a low voltage, pacing pulse by discharging the selected capacitor configuration across an extra-cardiovascular pacing electrode vector. In some examples, the medical device is configured to determine the capacitor configuration based on a measured impedance of the extra-cardiovascular pacing electrode vector.

20 Claims, 11 Drawing Sheets

(56) References Cited

U.S. PATENT DOCUMENTS

| | | |
|---|---|---|
| 7,751,885 B2 | 7/2010 | Bardy et al. |
| 8,412,320 B2 | 4/2013 | Ostroff et al. |
| 8,761,875 B2 * | 6/2014 | Sherwood ............ A61N 1/3906 361/503 |
| 2003/0105500 A1 | 6/2003 | Anderson et al. |
| 2014/0088656 A1 * | 3/2014 | Cabelka ................ A61N 1/362 607/2 |
| 2014/0243917 A1 | 8/2014 | Morley et al. |
| 2014/0330325 A1 | 11/2014 | Thompson-Nauman et al. |
| 2014/0330326 A1 | 11/2014 | Thompson-Nauman et al. |
| 2014/0330329 A1 | 11/2014 | Thompson-Nauman et al. |
| 2015/0306375 A1 | 10/2015 | Marshall et al. |
| 2015/0306410 A1 | 10/2015 | Marshall et al. |

OTHER PUBLICATIONS

Marshall et al., "Substernal Lead/Electrode Concepts", U.S. Appl. No. 62/089,417, filed Dec. 9, 2014, 28 pages.

* cited by examiner

EXTRA-CARDIOVASCULAR CARDIAC PACING SYSTEM

TECHNICAL FIELD

The disclosure relates generally to implantable medical devices and, in particular, to a system, device and method for delivering cardiac pacing pulses using extra-cardiovascular electrodes.

BACKGROUND

A variety of implantable medical devices (IMDs) for delivering a therapy, monitoring a physiological condition of a patient or a combination thereof have been clinically implanted or proposed for clinical implantation in patients. Some IMDs employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to position electrodes or other sensors at desired locations for delivery of electrical stimulation or sensing of physiological conditions. For example, electrodes or sensors may be carried along a distal portion of a lead that is extended subcutaneously, transvenously, or submuscularly. A proximal portion of the lead may be coupled to an implantable medical device housing, which contains circuitry such as signal generation circuitry and/or sensing circuitry.

Some IMDs, such as cardiac pacemakers or implantable cardioverter defibrillators (ICDs), provide therapeutic electrical stimulation to the heart of the patient via electrodes carried by one or more implantable leads and/or the housing of the pacemaker or ICD. The leads may be transvenous, e.g., advanced into the heart through one or more veins to position endocardial electrodes in intimate contact with the heart tissue. Other leads may be non-transvenous leads implanted outside the heart, e.g., implanted epicardially, pericardially, or subcutaneously. The electrodes are used to deliver electrical stimulation pulses to the heart to address abnormal cardiac rhythms.

IMDs capable of delivering electrical stimulation for treating abnormal cardiac rhythms typically sense signals representative of intrinsic depolarizations of the heart and analyze the sensed signals to identify the abnormal rhythms. Upon detection of an abnormal rhythm, the device may deliver an appropriate electrical stimulation therapy to restore a more normal rhythm. For example, a pacemaker or ICD may deliver low voltage pacing pulses to the heart upon detecting bradycardia or tachycardia using endocardial or epicardial electrodes. An ICD may deliver high voltage cardioversion or defibrillation shocks to the heart upon detecting fast ventricular tachycardia or fibrillation using electrodes carried by transvenous leads or non-transvenous leads. The type of therapy delivered and its effectiveness in restoring a normal rhythm depends at least in part on the type of electrodes used to deliver the electrical stimulation and their location relative to heart tissue.

SUMMARY

In general, the disclosure is directed to techniques for delivering extra-cardiovascular cardiac pacing pulses. A pacemaker or ICD operating according to the techniques disclosed herein measures a pacing electrode vector impedance and determines a capacitor configuration based on the measured impedance and pacing pulse duration. The capacitor configuration is selected so that an RC time constant of the discharging capacitor configuration across the pacing electrode vector results in a pacing pulse having a truncated pulse amplitude that is greater than a threshold amplitude. Extra-cardiovascular pacing may be delivered at a pacing pulse amplitude below a pain threshold of the patient with a pulse width long enough to deliver adequate energy to successfully pace the heart.

In one example, the disclosure provides an extra-cardiovascular medical device including an impedance measurement module configured to measure an impedance of an extra-cardiovascular pacing electrode vector when extra-cardiovascular pacing electrodes are electrically coupled to the medical device. The medical device includes a therapy delivery module having a capacitor array for producing a pacing pulse and a pacing control module coupled to the therapy delivery module and the impedance measurement module. The pacing control module is configured to control the impedance measurement module to measure the impedance of the extra-cardiovascular pacing electrode vector, determine a capacitor configuration based on the measured impedance, and control the therapy delivery module to deliver a cardiac pacing pulse by discharging the capacitor configuration for a predetermined pulse width across the extra-cardiovascular pacing electrode vector.

In another example, the disclosure provides a method performed by an extra-cardiovascular medical device including measuring an impedance of an extra-cardiovascular pacing electrode vector when extra-cardiovascular pacing electrodes are electrically coupled to the medical device, determining a capacitor configuration based on the measured impedance, and delivering a cardiac pacing pulse by discharging the first capacitor configuration for a predetermined pulse width across the extra-cardiovascular pacing electrode vector.

In another example, the disclosure provides a non-transitory, computer-readable storage medium comprising a set of instructions which, when executed by a control module of an extra-cardiovascular medical device, cause the medical device to measure an impedance of an extra-cardiovascular pacing electrode vector when extra-cardiovascular pacing electrodes are electrically coupled to the medical device, determine a capacitor configuration based on the measured impedance, and deliver a cardiac pacing pulse by discharging the capacitor configuration for a predetermined pulse width across the extra-cardiovascular pacing electrode vector.

In another example, the disclosure provides an extra-cardiovascular medical device including a therapy delivery module having a capacitor array including a plurality of capacitors for producing a pacing pulse and a pacing control module coupled to the therapy delivery module. The pacing control module is configured to select a first capacitor configuration comprising a first combination of the plurality of capacitors and control the therapy delivery module to select the first capacitor configuration by selectively enabling the first combination of the plurality of capacitors of the capacitor array. The pacing control module is configured to start a pulse width timing interval and control the therapy delivery module to start delivery of a cardiac pacing pulse by discharging the first capacitor configuration across an extra-cardiovascular pacing electrode vector coupled to the therapy delivery module. The pacing control module is further configured to obtain a sampled amplitude of the cardiac pacing pulse during the pulse width timing interval, compare the sampled amplitude to an amplitude threshold, and control the therapy delivery module to select a second capacitor configuration comprising a second combination of the plurality of capacitors different than the first combination and start discharging the second capacitor configuration across the extra-cardiovascular pacing electrode vector before the pulse width timing interval expires in response to the amplitude of the cardiac pacing pulse being less than or equal to the amplitude threshold.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
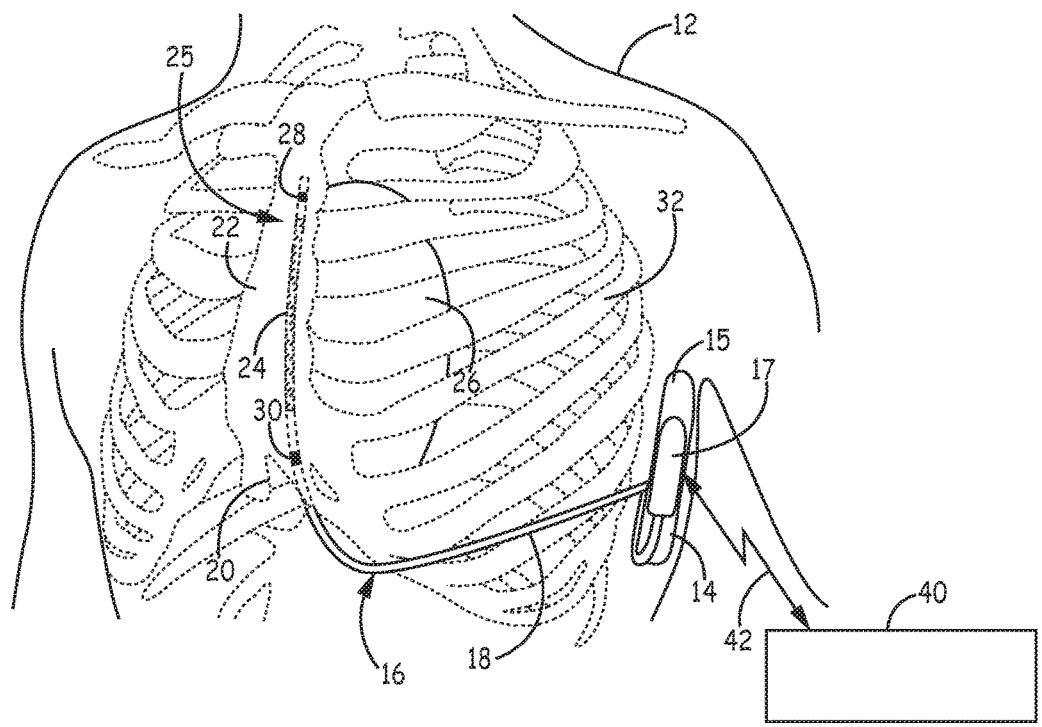
FIG. 1 is a conceptual diagram of a patient implanted with an example extra-cardiovascular IMD system that includes a subcutaneously implanted IMD coupled to an extra-cardiovascular sensing, pacing and cardioversion/defibrillation (CV/DF) lead.

In general, this disclosure describes techniques for delivering low voltage pacing pulses using extra-cardiovascular electrodes that are not directly contacting cardiac tissue. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but not in intimate contact with myocardial tissue. The term "low voltage" in reference to extra-cardiovascular pacing pulses refers to a voltage level that is below a pain threshold of a patient and may be on the order of 20 V or less in some examples.

Cardiac pacing is commonly delivered using electrodes in close or intimate contact with myocardial tissue such as endocardial electrodes or epicardial electrodes. Pacing pulses delivered using endocardial electrodes are typically up to a maximum of 8 V in pulse amplitude with a pulse width of 2.0 ms or less. A pacing pulse that successfully paces the heart might be 2.5 V in amplitude with a 0.5 ms pulse width, for example. The pulse amplitude and pulse width are selected to provide a pacing pulse having adequate energy to capture the heart, e.g., cause depolarization of the ventricles of the heart.

ICD systems have been proposed or are commercially available that utilize electrodes carried by subcutaneous or submuscular leads to sense electrocardiogram (ECG) signals and deliver high-energy shocks to cardiovert or defibrillate the heart. Electrodes carried by subcutaneous or submuscular leads may be used for delivering high-voltage, short-duration pulses during a post-shock recovery phase to treat asystole that may occur post-shock. Discomfort caused by these high voltage pacing pulses may be deemed acceptable post-shock in light of the life-saving treatment provided by shock delivery and post-shock, high-voltage pacing.

Such electrodes positioned subcutaneously or submuscularly are generally not used for delivering pacing therapies that are sustained over longer time periods or for conditions that are not immediately life threatening, e.g., for bradycardia pacing, anti-tachycardia pacing (ATP), or cardiac resynchronization therapy (CRT). The relatively high voltage amplitude required to successfully capture the heart when the electrodes are not in close contact with the myocardium may cause intolerable or unacceptable pain or discomfort to the patient. The high voltage is required in order to deliver enough energy within a limited pacing pulse width, e.g., 2 ms or less. This maximum pacing pulse width is limited by the decay rate of the pacing pulse which is dependent on the capacitance of the capacitor being discharged to deliver the pacing pulse and the impedance of the pacing electrode vector through which the capacitor is discharged For a given pulse width typically used with endocardial or epicardial electrodes, e.g., less than 2 ms, the pulse amplitude required to capture the heart using the same pulse width when pacing with extra-cardiovascular electrodes, such as subcutaneous or submuscular electrodes, may cross an acceptable pain threshold. A pacing pulse having a lower voltage amplitude that is not painful to the patient when delivered by extra-cardiovascular electrodes may require a relatively long pulse width that is likely to be beyond the capacity of a typical low voltage pacing capacitor due to the relatively fast decay rate of the pulse amplitude. A low voltage pacing capacitor may have a capacitance of 10 microfarads or less. Since a pacing pulse is delivered as the pacing capacitor is discharged across the pacing electrode vector, the pacing pulse amplitude may decay below an effective voltage amplitude before the required pacing pulse width is reached for successfully delivering the pacing pulse energy required to capture and pace the heart.

As disclosed herein, an implantable, extra-cardiovascular medical device system includes a therapy delivery module having an array of capacitors that are controlled by a pacing control module for delivering low voltage pacing pulses having a pulse width that is long enough, e.g., greater than 1.5 ms, to successfully pace the heart using a pulse amplitude that is below a pain threshold of the patient without requiring electrodes in direct contact with the myocardial or pericardial tissue. The pacing control module controls the decay rate of the pacing pulse by selecting a capacitor configuration that maintains the amplitude of the pacing pulse above a target amplitude for the duration of the pulse width. The techniques disclosed herein may be implemented in any implantable pacemaker or ICD and particularly in a pacemaker or ICD having extra-cardiovascular electrodes. The electrodes may be carried by a medical electrical lead extending from the pacemaker or ICD and/or carried by the housing of the pacemaker or ICD. The techniques disclosed herein are not necessarily limited to implantable systems and may be implemented in an external pacemaker or ICD using cutaneous surface electrodes or transcutaneous electrodes.

FIG. 1 is a conceptual diagram of a patient 12 implanted with an extra-cardiovascular IMD system 10 that includes a subcutaneously implanted IMD 14 coupled to an extra-cardiovascular sensing, pacing and cardioversion/defibrillation (CD/DF) lead 16. IMD 14 includes a housing 15 and connector assembly 17. IMD 14 acquires cardiac electrical signals, e.g., ECG signals, using electrodes carried by lead 16 and may be configured to deliver pacing pulses using extra-cardiovascular electrodes carried by lead 16. As will be described herein, IMD 14 includes a pacing control module that controls an array of pacing capacitors for delivering pacing pulses via extra-cardiovascular electrodes. The pacing pulses have a pulse amplitude that is less than the pain threshold of the patient and a pulse width that is long enough, e.g., greater than 1.5 ms or greater than 2.0 ms, to successfully pace the heart using extra-cardiovascular electrodes without causing unacceptable pain or discomfort to the patient. The cardiac electrical signals received by IMD 14 are used for determining the patient's heart rhythm and providing appropriate pacing therapy as needed, such as bradycardia pacing or ATP. IMD 14 is configured as an ICD in this example, capable of detecting shockable rhythms and delivering a CV/DF shock therapy via defibrillation electrode 24 carried by lead 16. In other examples, IMD 14 may be configured as a pacemaker for delivering low voltage pacing therapies without high voltage CV/DF shock therapy capability. In this case, lead 16 may be carry pacing and sensing electrodes, e.g., electrodes 28 and 30, without incorporating a defibrillation electrode 24 or defibrillation electrode 24 may be included and used as a return anode during cardiac pacing using electrode 28 or 30 as a cathode.

Lead 16 includes a proximal end 27 that is connected to IMD 14 and a distal portion 25 that carries electrodes 24, 28 and 30. Electrode 24 is a defibrillation electrode that may be used in combination with the conductive housing 15 of IMD 14 for delivering high voltage CV/DF shocks. All or a portion of housing 15 of IMD 14 may be formed of a conductive material, such as titanium or titanium alloy, and coupled to internal IMD circuitry to function as an electrode, sometimes referred to as a "CAN electrode." A shock vector pathway extends from defibrillation electrode 24 to housing 15, through the ventricular myocardium. Defibrillation electrode 24 is typically an elongated coil electrode having a relatively higher surface area than electrodes 28 and 30 but may be implemented as another type of electrode other than a coil electrode.

Electrodes 28 and 30 are referred to herein as pacing and sensing electrodes because they generally are used for delivering pacing pulses and sensing cardiac electrical signals. An ECG signal may be acquired using any combination of electrodes 28, 30 and housing 15. For example, IMD 14 may sense cardiac electrical signals using a sensing electrode vector between electrodes 28 and 30, a sensing electrode vector between electrode 28 and housing 15 or a sensing electrode vector between electrode 30 and housing 15 may be chosen. In some examples, a sensing electrode vector may even include defibrillation electrode 24, e.g., in conjunction with one or more of electrodes 28, 30, or housing 15. IMD 14 may include more than one sensing channel such that electrode sensing vectors may be selected two at a time by IMD 14 for monitoring for a shockable rhythm or a need for cardiac pacing.

Pacing pulses may be delivered using any combination of electrodes 24, 28, 30 and housing 15. The pacing electrode vector selected for delivering pacing pulses may be selected based on pacing electrode vector impedance measurements and capture threshold testing. For example, a pacing electrode vector may be selected from among electrodes 24, 28, 30 and housing 15 that has the lowest impedance and/or the lowest pulse width that captures the heart for a programmed pacing pulse amplitude. The pacing pulse amplitude may be programmed to be below a threshold for pain and discomfort, which may be based on individual patient testing and/or clinical data.

While three electrodes 24, 28 and 30 are shown along lead 16, lead 16 may carry more or fewer electrodes in other examples. In the example illustrated in FIG. 1, pacing and sensing electrodes 28 and 30 are separated from one another by defibrillation electrode 24. In other words, sensing electrode 28 is located distal to defibrillation electrode 24, and sensing electrode 30 is proximal to defibrillation electrode 24. In various examples, electrodes 28 and 30 may be carried along lead 16 at other locations than those shown but are generally positioned to acquire cardiac electrical signals having acceptable cardiac signal strength for sensing cardiac events, such as R-wave signals that occur upon depolarization of the ventricles and for delivering low voltage pacing pulses for successfully capturing the patient's heart 26. Pacing pulses may be delivered using any combination of electrodes 24, 28, 30 and/or housing 15, e.g., using electrodes 28 and 30 in a bipolar pair, using one of electrodes 28 or 30 paired with housing 15, using one of electrodes 28 or 30 paired with defibrillation electrode 24, using both or electrodes 28 and 30 tied together as a multi-polar cathode electrode paired with housing 15 or with defibrillation electrode 24, and so on.

Two or more electrodes used for delivering low voltage pacing pulses may be located at different locations along lead 16 in other examples. For instance, an electrode configuration including two pacing and sensing electrodes that are spaced apart along lead body 18 adjacent to each other without an intervening defibrillation electrode 24 may be used for delivering low voltage pacing pulses as disclosed herein. Two pacing and sensing electrodes may be positioned adjacent to each other at spaced apart locations in between two defibrillation electrodes as generally disclosed in commonly-assigned U.S. patent application Ser. No. 14/519,436 and U.S. patent application Ser. No. 14/695,255, both of which are incorporated herein by reference in their entirety.

In other examples, an extra-cardiovascular lead may include multiple defibrillation electrode segments, and multiple pacing and sensing electrodes may be disposed between the defibrillation electrode segments. The defibrillation electrode segments and pacing and sensing electrodes, which may be ring electrodes, may be carried by an undulating or zig-zagging distal portion of the lead body as generally disclosed in provisionally-filed U.S. Pat. Application No. 62/089,417, and may be utilized in conjunction with the pacing techniques disclosed herein. U.S. Pat. Application No. 62/089,417 is also incorporated herein by reference in its entirety. In still other examples, lead 16 may carry a single pace/sense electrode to serve as a pacing cathode electrode with housing 15 or with a defibrillation electrode 24 or any of the defibrillation electrodes or defibrillation electrode segments shown and described in the above-incorporated references, serving as the return anode electrode.

In other examples, dedicated pacing electrodes and separate, dedicated sensing electrodes may be carried by lead 16 or another lead coupled to IMD 14. It is understood that one or more leads may be coupled to IMD 14 for connecting at least one pacing and sensing electrode to IMD 14 for monitoring cardiac electrical signals, and delivering low voltage pacing pulses and at least one defibrillation electrode and for delivering CV/DF shock therapy when IMD 14 is configured as an ICD. Pacing therapies that may be delivered by IMD 14 may include bradycardia pacing, ATP, CRT and/or post-shock pacing for treating bradycardia or asystole after a CV/DF shock.

Lead 16 is illustrated in FIG. 1 as being implanted at least partially in a substernal location, e.g., between the heart 26 and ribcage 32 or sternum 22. In one such configuration, the proximal portion of lead 16 extends subcutaneously from IMD 14 (which is implanted near a midaxillary line on the left side of patient 12) toward sternum 22. At a location near xiphoid process 20, lead 16 bends or turns superiorly and distal portion 25 of lead 16, which carries electrodes 24, 28 and 30, extends substernally, under or below the sternum 22 in the anterior mediastinum 36.

Figure 2:
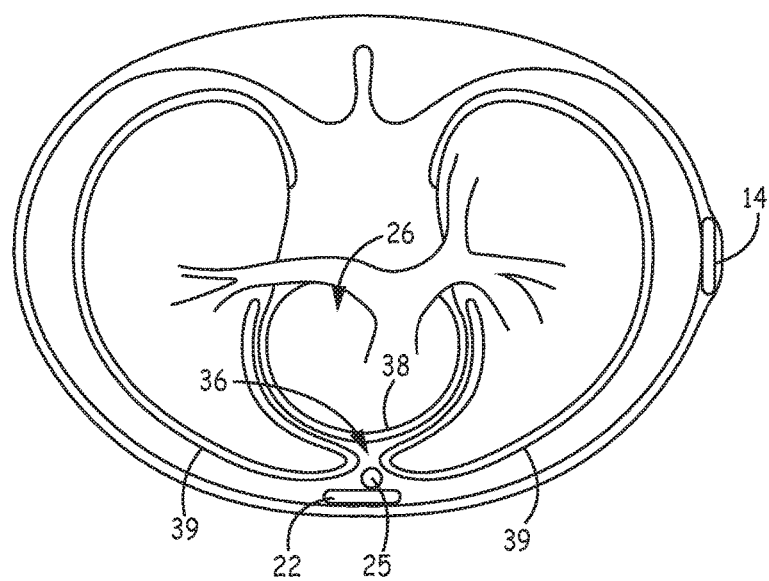
FIG. 2 is a transverse view of a patient depicting an alternative, substernal location of the extra-cardiovascular lead of FIG. 1.

FIG. 2 is a transverse view of patient 12 showing the distal portion 25 of lead 16 extending substernally, e.g., at least partially in or adjacent to the anterior mediastinum 36. Anterior mediastinum 36 is bounded laterally by pleurae 39, posteriorly by pericardium 38, and anteriorly by sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), adipose tissue, some lymph vessels, lymph glands, substernal musculature (e.g., transverse thoracic muscle), branches of the internal thoracic artery, the thymus gland, and the internal thoracic vein. In one example, the distal portion of lead 16 extends along the posterior side of sternum 22 substantially within the loose connective tissue and/or substernal musculature of anterior mediastinum 36. Lead 16 may be at least partially implanted in other extra-cardiovascular, intrathoracic locations, e.g., along ribcage 32 or along or adjacent to the perimeter of the pericardium 38 or within the pleural cavity.

IMD 14 may also be implanted at other subcutaneous or submuscular locations on patient 12, such as further posterior on the torso toward the posterior axillary line, further anterior on the torso toward the anterior axillary line, in a pectoral region, or at other locations of patient 12. In instances in which IMD 14 is implanted pectorally, lead 16 would follow a different path, e.g., across the upper chest area and inferior along sternum 22. When the IMD 14 is implanted in the pectoral region, the system 10 may include a second lead that extends along the left side of the patient and includes a defibrillation electrode and/or one or more pacing electrodes positioned along the left side of the patient to function as an anode or cathode of a therapy delivery vector including another electrode located anteriorly for delivering electrical stimulation to heart 26 positioned there between.

In other examples, lead 16 may be implanted at other extra-cardiovascular locations. For instance, lead 16 may be implanted subcutaneously or submuscularly, between the skin and the ribcage 32 or between the skin and sternum 22. Lead 16 extends subcutaneously from IMD 14 toward xiphoid process 20 as shown in FIG. 1, but instead of extending substernally, lead 16 may bend or turn at a location near xiphoid process 20 and extend subcutaneously or submuscularly superior, substantially parallel to sternum 22. The distal portion 25 of lead 16 may be parallel over sternum 22 or laterally offset from sternum 22, to the left or the right. In other examples, the distal portion 25 of lead 16 may be angled laterally away from sternum 22, either to the left or the right, such that the distal portion 25 extends non-parallel to sternum 22.

In another example, IMD 14 may be implanted subcutaneously outside the ribcage 32 in an anterior medial location. Lead 16 may be tunneled subcutaneously into a location adjacent to a portion of the latissimus dorsi muscle of patient 12, from a medial implant pocket of IMD 14 laterally and posteriorly to the patient's back to a location opposite heart 26 such that the heart 26 is generally disposed between the IMD 14 and electrodes 24, 28 and 30. The techniques disclosed herein for generating low voltage pacing pulses for pacing the heart using extra-cardiovascular electrodes are not limited to a particular subcutaneous, submuscular, suprasternal, substernal or intra-thoracic location of the extra-cardiovascular electrodes.

Referring again to FIG. 1, lead 16 includes an elongated lead body 18 that carries the electrodes 24, 28 and 30 and insulates one or more elongated electrical conductors (not illustrated) that extend from a respective electrode 24, 28 and 30 through the lead body 18 to a proximal connector (not shown) that is coupled to IMD 14 at lead proximal end 27. Lead body 18 may be formed from a non-conductive material, such as silicone, polyurethane, fluoropolymers, or mixtures thereof or other appropriate materials, and is shaped to form one or more lumens within which the one or more conductors extend. The conductors are electrically coupled to IMD circuitry, such as a therapy delivery module and an electrical sensing module, via connections in IMD connector assembly 17 that includes a connector bore for receiving the proximal connector of lead 16 and associated electrical feedthroughs crossing IMD housing 15. The electrical conductors transmit electrical stimulation therapy from a therapy delivery module within IMD 14 to one or more of electrodes 24, 28, and 30, and transmit cardiac electrical signals from one or more of electrodes 24, 28, and 30 to the sensing module within IMD 14.

Housing 15 forms a hermetic seal that protects internal electronic components of IMD 14. As indicated above, housing 15 may function as a "CAN electrode" since the conductive housing or a portion thereof may be electrically coupled to internal circuitry to be used as an indifferent or ground electrode during cardiac signal sensing or during electrical stimulation therapy delivery. As will be described in further detail herein, housing 15 may enclose one or more processors, memory devices, transmitters, receivers, sensors, sensing circuitry, therapy circuitry and other appropriate components.

The example IMD system 10 of FIG. 1 is illustrative in nature and should not be considered limiting of the techniques described in this disclosure. The techniques disclosed herein may be implemented in numerous ICD or pacemakers operating with electrode configurations that include extra-cardiovascular electrodes for delivering cardiac pacing pulses. The IMD system 10 is referred to as an extra-cardiovascular IMD system because lead 16 is a non-transvenous lead, positioned outside the blood vessels, heart 26 and pericardium 38.

An external device 40 is shown in telemetric communication with IMD 14 by a communication link 42. External device 40 may include a processor, display, user interface, telemetry unit and other components for communicating with IMD 14 for transmitting and receiving data via communication link 42. Communication link 42 may be established between IMD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from IMD 14 and to program operating parameters and algorithms in IMD 14 for controlling IMD functions. External device 40 may be used to program cardiac rhythm detection parameters and therapy control parameters used by IMD 14. Data stored or acquired by IMD 14, including physiological signals or associated data derived therefrom, results of device diagnostics, and histories of detected rhythm episodes and delivered therapies, may be retrieved from IMD 14 by external device 40 following an interrogation command. External device 40 may alternatively be embodied as a home monitor or hand-held device.

Figure 3:
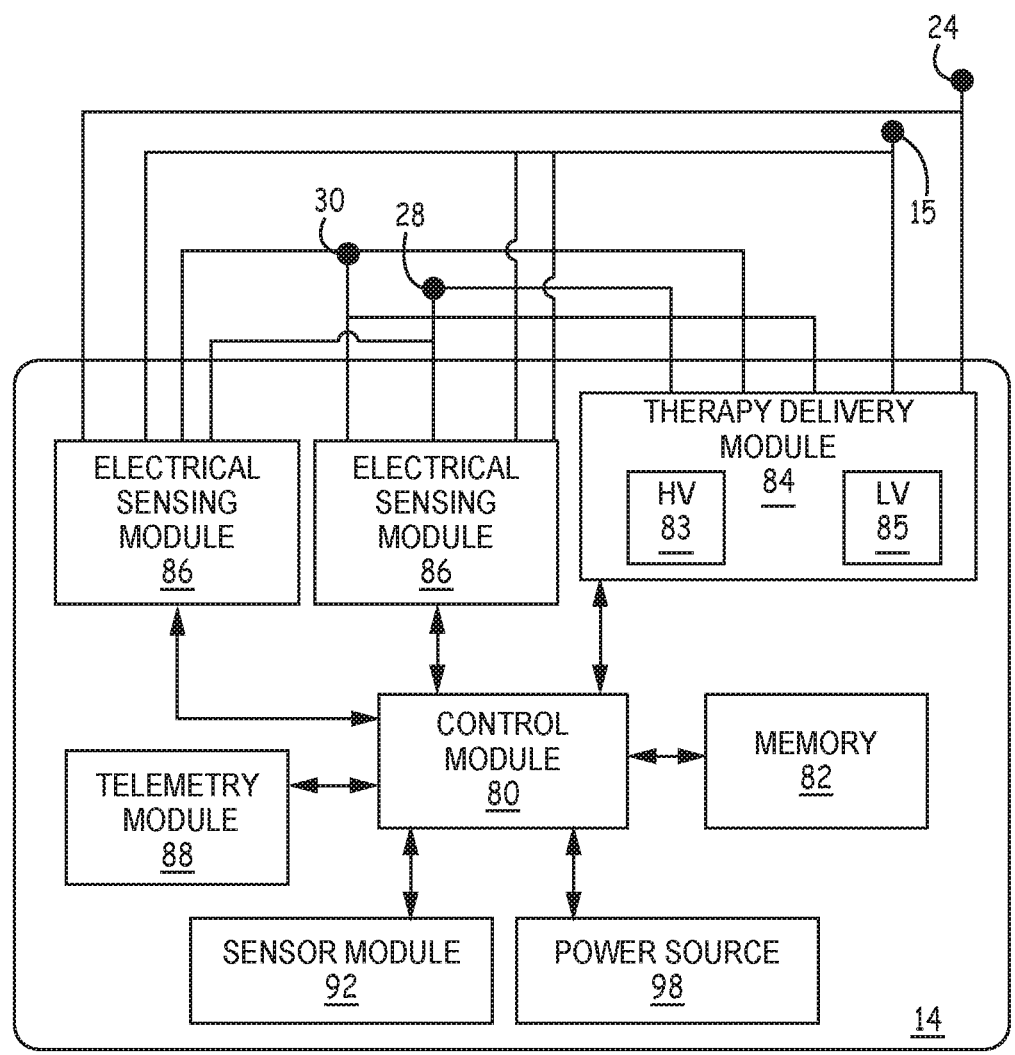
FIG. 3 is a schematic diagram of the IMD of FIG. 1 according to one example.

FIG. 3 is a schematic diagram of IMD 14 according to one example. The electronic circuitry enclosed within housing 15 includes software, firmware and hardware that cooperatively monitor one or more cardiac electrical signals, determine when a pacing therapy is necessary, and deliver prescribed pacing therapies as needed. When IMD 14 is configured as an ICD as illustrated herein, the software, firmware and hardware is also configured to determine when a CV/DF shock is necessary and deliver prescribed CV/DF shock therapies. IMD 14 may be coupled to a lead, such as lead 16 shown in FIG. 1, carrying extra-cardiovascular electrodes 24, 28 and 30, for delivering pacing therapies, CV/DF shock therapies and sensing cardiac electrical signals.

IMD 14 includes a control module 80, memory 82, therapy delivery module 84, electrical sensing module 86, telemetry module 88, impedance measurement module 90 and an optional sensor module 92. A power source 98 provides power to the circuitry of IMD 14, including each of the modules 80, 82, 84, 86, 88, 90 and 92 as needed. Power source 98 may include one or more energy storage devices, such as one or more rechargeable or non-rechargeable batteries. Power source 98 is coupled to low voltage (LV) and high voltage (HV) charging circuits included in therapy delivery module 84 for charging LV and HV capacitors, respectively, included in therapy delivery module 84 for generating therapeutic electrical stimulation pulses.

The functional blocks shown in FIG. 3 represent functionality included in IMD 14 and may include any discrete and/or integrated electronic circuit components that implement analog and/or digital circuits capable of producing the functions attributed to IMD 14 herein. For example, the modules may include analog circuits, e.g., amplification circuits, filtering circuits, and/or other signal conditioning circuits. The modules may also include digital circuits, e.g., analog-to-digital converters, digital signal processors (DSPs), combinational or sequential logic circuits, integrated circuits, application specific integrated circuits (ASICs), memory devices, etc. As used herein, the term "module" refers to an ASIC, an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the IMD and by the particular detection and therapy delivery methodologies employed by the IMD. Providing software, hardware, and/or firmware to accomplish the described functionality in the context of any modern IMD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory, computer-readable media storing instructions that, when executed by one or more processing circuits, cause control module 80 or other IMD modules to perform various functions attributed to IMD 14 or those IMD modules. The non-transitory computer readable media storing the instructions may include any of the media listed above.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware, firmware or software components. Rather, functionality associated with one or more modules may be performed by separate hardware, firmware or software components, or integrated within common hardware, firmware and/or software components. For example, pacing therapy control operations performed by control module 80 may be implemented in a processor executing instructions stored in memory 82.

Control module 80 communicates with therapy delivery module 84 and electrical sensing module 86 for sensing cardiac electrical activity, detecting cardiac rhythms, and controlling delivery of cardiac electrical stimulation therapies in response to sensed cardiac signals. Therapy delivery module 84 and electrical sensing module 86 are electrically coupled to electrodes 24, 28, and 30 carried by lead 16 (shown in FIG. 1) and the housing 15, which may function as a common or ground electrode.

Electrical sensing module 86 is selectively coupled to electrodes 28, 30 and housing 15 in order to monitor electrical activity of the patient's heart. Electrical sensing module 86 may additionally be selectively coupled to electrode 24. Sensing module 86 is enabled to selectively monitor one or more sensing vectors selected from the available electrodes 24, 28, 30 and 15. For example, sensing module 86 may include switching circuitry for selecting which of electrodes 24, 28, 30 and housing 15 are coupled to sense amplifiers or other cardiac event detection circuitry included in sensing module 86. Switching circuitry may include a switch array, switch matrix, multiplexer, or any other type of switching device suitable to selectively couple sense amplifiers to selected electrodes. The cardiac event detection circuitry within electrical sensing module 86 may include one or more sense amplifiers, filters, rectifiers, threshold detectors, comparators, analog-to-digital converters (ADCs), or other analog or digital components.

In some examples, electrical sensing module 86 includes multiple sensing channels for acquiring cardiac electrical signals from multiple sensing electrode vectors selected from electrodes 24, 28, 30 and housing 15. Each sensing channel may be configured to amplify, filter and rectify the cardiac electrical signal received from selected electrodes coupled to the respective sensing channel to improve the signal quality for sensing cardiac events, e.g., R-waves.

Each sensing channel includes cardiac event detection circuitry for sensing cardiac events from the received cardiac electrical signal developed across the selected electrodes 24, 28, 30 and/or 15. Cardiac event sensing thresholds used by each sensing channel may be automatically adjusted according to sensing control parameters, which may be stored in memory 82. Each sensing channel senses a cardiac event when the respectively received cardiac electrical signal crosses the auto-adjusting cardiac event sensing threshold.

Each time the received cardiac electrical signal crosses the sensing threshold for a given channel, a cardiac sensed event signal is produced and passed to control module 80. For example, R-wave sensed event signals may be passed to control module 80 when a received cardiac electrical signal crosses an R-wave sensing threshold. Sensed event signals produced by electrical sensing module 86 may be used by control module 80 for detecting a shockable rhythm and/or for detecting a need for pacing. For example, control module 80 may respond to sensed event signals by setting pacing escape intervals for controlling the timing of pacing pulses delivered by therapy delivery module 84. In addition to the sensed cardiac event signals, electrical sensing module 86 may output a digitized ECG signal for use by control module 80 in detecting/confirming tachycardia, e.g., via a morphology or wavelet analysis.

Therapy delivery module 84 includes an LV therapy delivery module 85 for delivering low voltage pacing pulses using an extra-cardiovascular pacing electrode vector selected from electrodes 24, 28, 30 and housing 15. The LV therapy delivery module includes an array of capacitors that are selectably controlled by control module 80 to provide low voltage, long pulse width pacing pulses having a truncated pulse amplitude at pulse termination that is greater than a threshold amplitude. LV capacitors included in the LV therapy delivery module 85 are charged to a voltage according to a programmed pacing pulse amplitude by an LV charging circuit (not shown in FIG. 3) included in therapy delivery module 84. At an appropriate time, the LV therapy delivery module 85 couples a selected capacitor configuration to a pacing electrode vector to discharge the capacitor configuration over a predetermined pacing pulse width.

As described below, a pacing control module included in control module 80 may be configured to receive a feedback signal from LV therapy delivery module 85. The feedback signal indicates the amplitude of the pacing pulse as it is decaying over the pacing pulse width during capacitor discharge. If the pulse amplitude falls to a threshold amplitude before the end of the pulse width, the pacing control module may be configured to adjust the output signal of the LV therapy delivery module 85 by enabling at least one additional capacitor in the capacitor array of LV therapy delivery module 85. By enabling an additional capacitor(s), the voltage amplitude of the pacing pulse is maintained at or above a minimum acceptable amplitude during the relatively long discharge period defined by the pacing pulse width. The minimum acceptable amplitude is the minimum amplitude at which capture and successful pacing of the heart is highly probable.

Impedance measurement module 90 may be electrically coupled to the available electrodes 24, 28 and 30 and housing 15 for performing impedance measurements of a selected pacing electrode vector. Control module 80 may control impedance measurement module 90 to perform impedance measurements prior to pacing pulse delivery and/or during a pacing pulse delivery. For example, control module 80 may pass a signal to impedance measurement module 90 to initiate an impedance measurement for a selected pacing electrode vector. Impedance measurement module 90 is configured to apply a drive or excitation current across a selected pacing electrode vector and determine the resulting voltage. The voltage signal may be used directly as the impedance measurement or impedance may be determined from the applied current and the measured voltage. The impedance measurement is passed to control module 80 for use in selecting a capacitor configuration for delivering pacing pulses. The capacitor configuration selected based on the impedance measurement may be the initial capacitor configuration used to deliver a pacing pulse or an adjusted capacitor configuration used to adjust the pacing pulse amplitude in real-time during a pacing pulse. Capacitor configuration data is passed from control module 80 to LV therapy delivery module 85 for use in delivering pacing pulses using the selected capacitor configuration as described in greater detail below.

Therapy delivery module 84 may additionally include HV therapy delivery module 83 including one or more HV output capacitors. When a shockable rhythm is detected, the HV capacitors are charged to a pre-programmed voltage level by a HV charging circuit, which may include one or more transformers, switches, diodes, or the like. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy CV/DF shocks using defibrillation electrode 24 and housing 15. High energy CV/DF shocks are generally on the order of at least 5 Joules and more commonly on the order of 20 Joules or higher. In contrast, low voltage pacing pulses delivered using extra-cardiovascular electrodes may be on the order of 0.1 Joules or less, whereas pacing pulses delivered using endocardial electrodes or epicardial electrodes may be on the order of microJoules, e.g., 2 microJoules to 5 microJoules for a typical pacing pulse that is 2V in amplitude, 0.5 ms in pulse width and applied across a pacing electrode vector impedance of 400 to 1,000 ohms.

Sensor module 92 may include additional sensors for monitoring the patient and/or for controlling therapy delivery. For example, sensor module 92 may include an activity sensor, a posture sensor, a heart sound sensor, or other physiological sensor(s) for monitoring the patient and making therapy delivery decisions. In various examples, rate responsive pacing may be provided based on a patient activity signal. The pacing rate delivered using extra-cardiovascular electrodes may be increased according to an increased metabolic demand of the patient as evidenced by the patient activity signal. A decision to deliver ATP pulses (using extra-cardiovascular electrodes, e.g., electrodes 24, 28, 30 and/or housing 15 or other extra-cardiovascular electrode configurations referred to herein) or shock therapy (using defibrillation electrode 24 and housing 15) may be based in part on physiological sensor signals in addition to the cardiac electrical signal.

Control parameters utilized by control module 80 may be programmed into memory 82 via telemetry module 88. For example, the pacing pulse width and pacing pulse amplitude may be programmable parameters. Control module 80 may utilize the programmed pacing pulse width and pacing pulse amplitude for controlling the selection and charging of LV capacitors included in LV therapy delivery module 85. Telemetry module 88 includes a transceiver and antenna for communicating with external device 40 (shown in FIG. 1) using RF communication as described above. Under the control of control module 80, telemetry module 88 may receive downlink telemetry from and send uplink telemetry to external device 40. In some cases, telemetry module 88 may be used to transmit and receive communication signals to/from another medical device implanted in patient 12.

Figure 4:
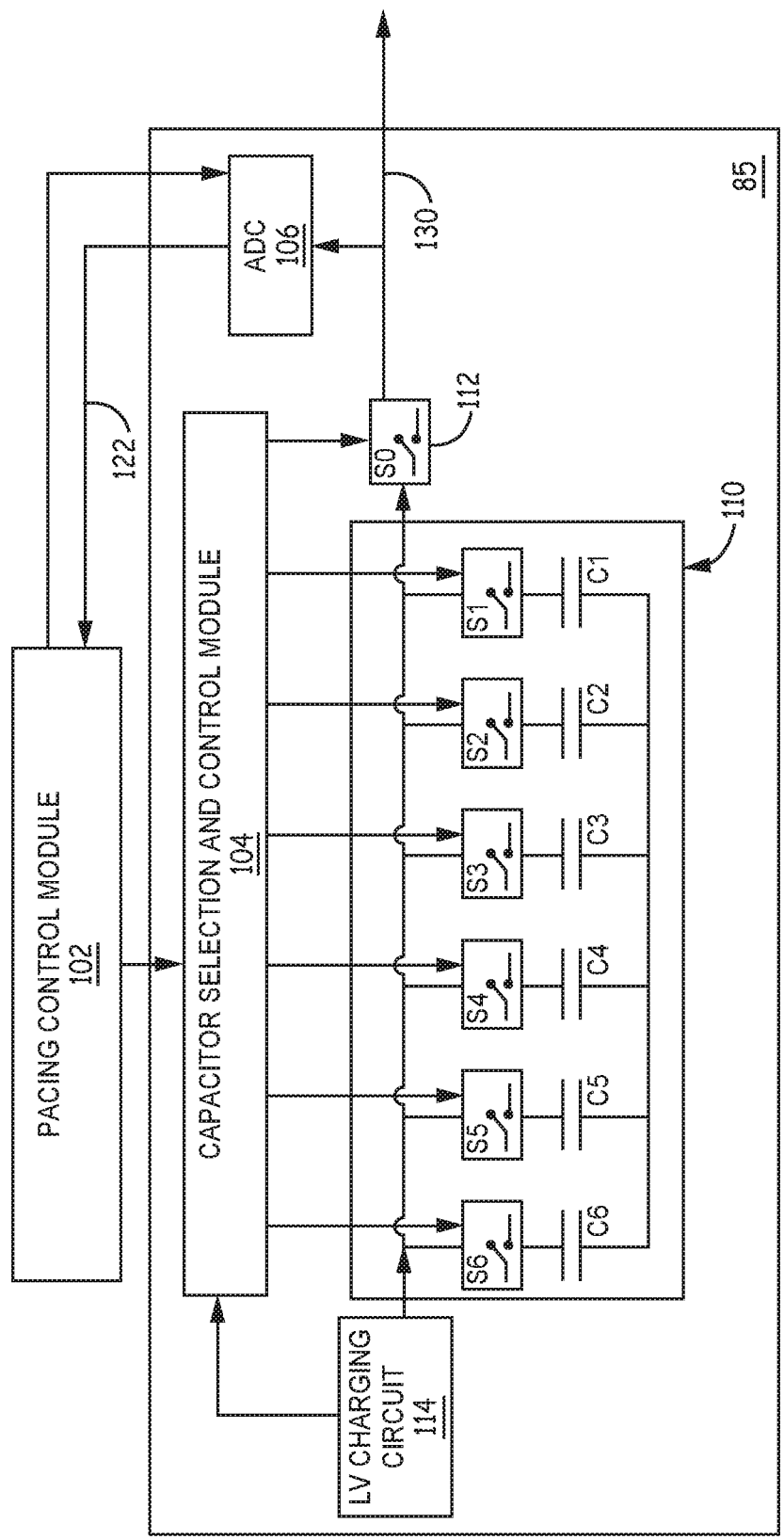
FIG. 4 is a schematic diagram of a pacing control module and a therapy delivery module included in IMD 14.

FIG. 4 is a schematic diagram of a pacing control module 102 included in control module 80 and the LV therapy delivery module 85 included in therapy delivery module 84. LV therapy delivery module 85 includes a capacitor selection and control module 104 and a capacitor array 110 including multiple parallel capacitors C1 through Cn, where n is six in the example shown. Capacitor array 110 includes multiple switches S1 through Sn (S6 in the example shown) that are controlled by capacitor selection and control module 104 to selectively enable capacitors C1 through C6 for pacing pulse delivery. Switches S1 through S6 each enable a respective one of capacitors C1 through C6 when closed by coupling the enabled capacitor to pacing pulse output signal line 130 when switch 112 is also closed.

While six capacitors are shown, capacitor array 110 may include more or fewer capacitors, which may depend on the requirements of the particular pacing application, and available volume in the housing 15. Capacitors C1 through C6 may be provided with a capacitance of 20 microfarads in one example but capacitances greater than or less than 20 microfarads may be used, e.g., 10 microfarads to 40 microfarads. Capacitors C1 through C6 may all have the same capacitance values or different values to provide different selectable effective capacitances for achieving various RC time constants of the pacing discharge circuit and desired ranges of pacing pulse widths for an expected range of pacing electrode vector impedance.

A longer effective pulse width is possible when two or more of capacitors C1 through C6 are selected together in parallel than when any one is selected alone. The capacitors in parallel have an effective capacitance equal to the sum of the parallel capacitances for a total capacitance greater than any one of the capacitors selected alone. The greater capacitance increases the RC time constant for a given pacing electrode vector impedance. A higher capacitance and RC time constant decreases the decay rate of the pacing pulse and increases the maximum possible pacing pulse width for a given programmed pulse amplitude and pacing electrode vector impedance. The longer pulse width results in greater pulse energy delivered across the pacing electrode vector for capturing the heart. If the pulse decays too rapidly, the pulse amplitude at the expiration of the pulse width may be too low to successfully capture the heart. In order to achieve capture using a non-painful, leading edge voltage amplitude of an extra-cardiovascular pacing pulse, a relatively long pulse width, e.g. greater than 2.0 ms, may be needed over which the decaying pulse amplitude is maintained above a minimum threshold so that the total delivered pulse energy is above the capture threshold of the heart.

In one example, C1 has a higher capacitance than capacitors C2 through C6 to provide a relatively long decay time when C1 is selected alone for pacing pulse delivery. C2 through C6 may be provided with lower capacitance values than C1 so that capacitor configurations can be selected having higher effective capacitance values at desired increments greater than the C1 capacitance.

Capacitor selection and control module 104 controls LV charging circuit 114 to charge capacitor array 110 for supplying pacing pulse energy. LV charging circuit 114 charges capacitor array 110 to a voltage level according to a programmed pacing pulse amplitude. Power source 98 may provide regulated power to LV charging circuit 114. LV charging circuit 114 may be controlled to charge all capacitors C1-C6 or only selected ones of capacitors C1-C6 to a voltage required for generating a pacing pulse having a leading edge voltage amplitude at the programmed pulse amplitude. LV charging circuit 114 includes a charge pump to charge the parallel capacitors of array 110 when signaled by capacitor selection and control module 104, which also closes switches S1 through S6 to enable charging of respective capacitors C1 through C6. LV charging circuit 114 may include a voltmeter or other indicator for providing a feedback signal to the charge pump during charging and a comparator to determine when charging is complete, e.g., when the charge reaches the programmed pulse amplitude.

LV charging circuit 114 will monitor and control the charging of capacitors C1-C6 and may pass a control signal to capacitor selection and control module 104 for controlling switch 112 to be open while LV charging circuit 114 is charging to uncouple capacitor array 110 from output signal line 130. LV charging circuit 114 may pass a charge completion signal to capacitor selection and control module 104 when the capacitor selection is charged to a desired voltage. Switch 112 may be closed by capacitor selection and control module 104 after charge completion and when it is time to start pacing pulse delivery.

Capacitor selection and control module 104 receives control signals and instructions from pacing control module 102 including capacitor configuration data, pacing pulse timing data, and pacing pulse amplitude and pulse width. In response to a signal from pacing control module 102, capacitor selection and control module 104 enables a selected capacitor configuration of capacitor array 110, by closing respective switches S1 to S6, and couples the selected capacitor configuration to output signal line 130 via switch 112 to discharge the selected capacitor configuration across a pacing electrode vector coupled to output signal line 130. The capacitor selection and control module 104 uncouples capacitor array 110 from output signal line 130 by opening switch 112 at the expiration of a programmed pacing pulse width. The pacing pulse is terminated when switch 112 is opened.

In some examples, LV therapy delivery module 85 includes an analog-to-digital converter (ADC) 106 for sampling the pacing pulse amplitude in real-time and providing a digital feedback signal of the sampled amplitude to pacing control module 102 on signal line 122. During the pacing pulse, pacing control module 102 enables ADC 106 to sample the pacing pulse output signal on output signal line 130 at a desired sampling rate, e.g., every 2 ms, throughout the pacing pulse width. ADC 106 may be enabled to sample the pacing pulse amplitude from the start of the pacing pulse when switch 112 is enabled (closed) until the end of the pacing pulse when switch 112 is disabled (opened). In other examples, ADC 106 may be enabled at a predetermined time interval after the start of the pacing pulse, e.g. after a first portion of the pacing pulse width.

The ADC 106 does not disrupt the pacing pulse but samples the pulse amplitude and converts the analog pulse amplitude to a digital representation for processing by pacing control module 102. Pacing control module 102 monitors the sampled pacing pulse amplitude received from ADC 106 during pacing pulse delivery by comparing the sample points to a pre-determined amplitude threshold or to an expected amplitude based on predicted values. In one example, the sample points are compared to an amplitude threshold set as a percentage of the programmed pacing pulse amplitude, e.g., 50% of the programmed pacing pulse amplitude.

If the pacing pulse amplitude falls below the amplitude threshold, the pacing control module 102 selects a second capacitor configuration having an appropriate capacitance and stored energy to compensate for the decayed charge of the initial capacitor configuration. By enabling a second capacitor configuration that is holding the charged voltage amplitude, the pacing pulse amplitude is increased during pulse delivery, preserving the effective longevity of the pacing pulse width and delivered energy required for capturing of the heart. In this way, the capacitor selection can be reconfigured during a single pacing pulse to increase the pacing pulse voltage amplitude in the event of a faster than anticipated decay rate. The capacitor selection and control module 104 is capable of managing the switches S1 to S6 to achieve real-time capacitor reconfiguration during a pacing pulse. The sampling interval, e.g., 2 ms or less, may be adjusted as needed to enable real-time adjustment of the capacitor configuration from an initial capacitor configuration to a second capacitor configuration during the pacing pulse to maintain the pulse amplitude above a minimum acceptable threshold.

In one example, the second capacitor configuration is selected by passing a control signal to capacitor selection and control module 104 to enable at least one capacitor of capacitor array 110 that was not included in the initial capacitor configuration. The capacitor(s) of the second capacitor configuration restore a higher pacing pulse amplitude to ensure the programmed pulse width and required total pulse energy to capture the heart is achieved, even under changing in vivo conditions such as changing impedance along the pacing vector.

All or at least a portion of capacitors C1 through C6 are charged prior to pacing pulse delivery. At least one capacitor more than the number of capacitors being selected in the initial capacitor configuration may be charged prior to pacing pulse delivery. In response to a control signal from pacing control module 102, capacitor selection and control module 104 reconfigures the initial capacitor configuration to a second capacitor configuration that includes at least one capacitor not used in the initial capacitor configuration.

In an illustrative example, C1, C2 and C3 may be initially enabled by capacitor selection and control module 104. Capacitors C1, C2, and C3 are collectively discharged across the pacing electrode vector via output signal line 130 to begin delivery of the pacing pulse at the desired pulse amplitude. The output of capacitors C1, C2, and C3 decays over time during capacitor discharge. If pacing control module 102 determines that the sampled pulse amplitude has reached or fallen below a pre-determined threshold during the pacing pulse, pacing control module 102 passes a signal to capacitor selection and control module 104 to couple at least one new capacitor to pacing pulse output signal line 130. For example, capacitor selection and control module 104 may enable capacitor C4 via switch S4. By adding a capacitor C4 to the previously-enabled, discharging capacitors C1, C2 and C3 during pacing pulse delivery, the pulse amplitude may be maintained above a minimum pulse amplitude throughout the pacing pulse width. C1, C2 and C3 may be disabled or switched off when C4 is enabled to ensure all the energy from C4 is directed to the output signal line 130 via switch 112. In other examples, circuitry such as one or more diodes may be included in capacitor array 110 to prevent charge distribution from newly-enabled capacitor (s) to the partially-discharged initial capacitor(s) and promote current flow produced by all discharging capacitors to output line 130 so that all capacitors discharge across the pacing electrode vector.

The added capacitor C4 in the second capacitor configuration may be previously charged, prior to pacing pulse delivery. Frequent sampling of the pulse amplitude may allow an amplitude threshold crossing to be predicted and thereby allow charging of additional capacitors on an as needed basis. Pacing control module 102 may trigger capacitor selection and control module 104 to charge an additional capacitor(s), C4 in this example, in preparation for enabling a second capacitor configuration if needed.

Capacitor selection and control module 104 may control which of capacitors C1 through C6 are re-charged after delivering a pacing pulse. In some examples, all available capacitors C1 through C6 are fully charged between pacing pulses and remain charged if not used for pacing pulse delivery. The charge of any unused capacitors may be topped off between pacing pulses. In other cases, the number of capacitors beyond the initial capacitor configuration that are charged and available for adding to the discharge circuit during pacing pulse delivery may include all the remaining available capacitors or a preset number of additional capacitors, e.g., one to three additional capacitors. In other examples the number of additional capacitors may depend on the pulse width. To illustrate, for very long pulse widths, e.g., greater than 10 ms, all available capacitors may be charged. For relatively short pulse widths, e.g., less than 5 ms, one additional capacitor may be charged. For moderate pulse widths, e.g., from 5 ms to 10 ms, two additional capacitors may be charged. Since the pulse amplitude may be more likely to fall below a minimum threshold amplitude before the end of the pacing pulse when longer pulse widths are used, a greater number of additional capacitors may be charged to be available during pacing pulse delivery. The number of additional capacitors available may be limited by how many are being used in the initial capacitor configuration.

Figure 5:
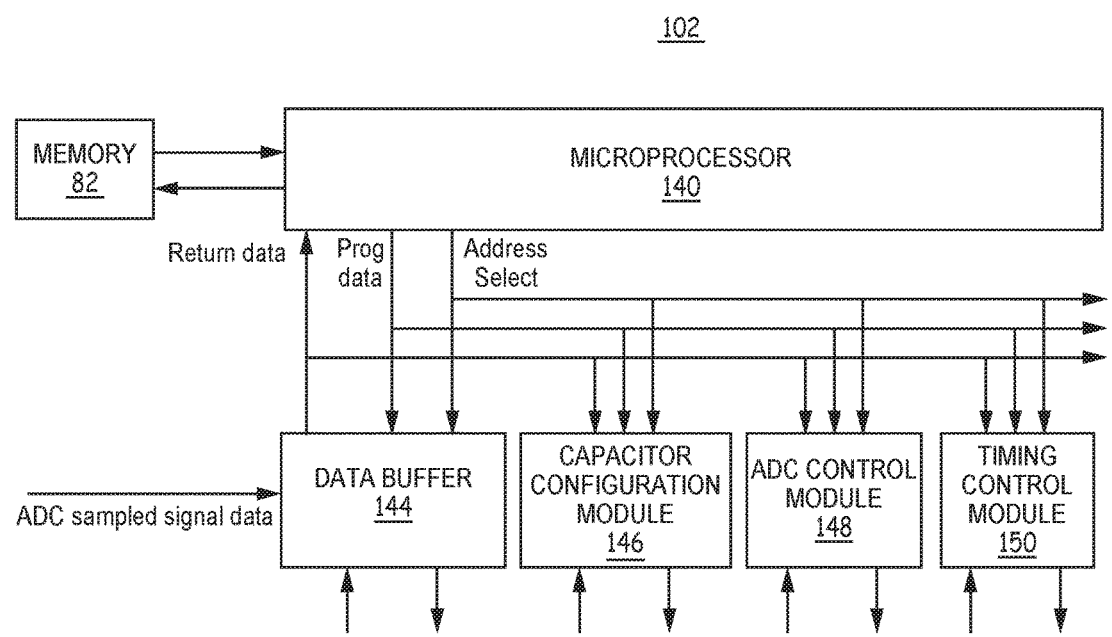
FIG. 5 is a schematic diagram of the pacing control module of FIG. 4.

FIG. 5 is a schematic diagram of pacing control module 102 included in control module 80 and capable of accessing instructions stored in memory 82. Pacing control module 102 may include a microprocessor 140, data buffer 144, capacitor configuration module 146, ADC control module 148 and timing control module 150. Microprocessor 140 may be configured to execute instructions stored in memory 82 for selecting an initial capacitor configuration for delivering a pacing pulse and for automatically adjusting the capacitor configuration during the pacing pulse.

Microprocessor 140 provides capacitor configuration data to capacitor configuration module 146 which passes the capacitor configuration data to the capacitor selection and control module 104 of LV therapy delivery module 85 (FIG. 4). Microprocessor 140 may also pass instructions to ADC control module 148. ADC control module 148 may be configured to control the sampling rate and sampling time period(s) of ADC 106 (FIG. 4). Pulse amplitude sample points are received by data buffer 144 from ADC 106 and passed to microprocessor 140. Microprocessor 140 compares the sampled amplitude values to an amplitude threshold. Based on this comparison, microprocessor 140 determines if a capacitor configuration change is required. If the sampled pulse amplitude is at or below the threshold, a capacitor configuration adjustment is needed to maintain the pulse amplitude above a minimum acceptable amplitude throughout the programmed pulse width.

Microprocessor 140 passes new configuration data to capacitor configuration module 146 in response to the sampled amplitude falling to or below the threshold amplitude. Capacitor configuration module 146 in turn passes the new configuration data to capacitor selection and control module 104 of LV therapy delivery module 85, e.g., on the next clock signal. The capacitor configuration is now set until another reconfiguration occurs. In this way, the pacing pulse output signal amplitude is adjusted by changing the capacitor configuration during delivery of the pacing pulse, i.e., before the pacing pulse width expires, in real-time.

Data buffer 144 may receive impedance data from impedance measurement module 90. Microprocessor 140 may retrieve the impedance measurement data for use in determining an initial capacitor configuration and/or in selecting an adjusted capacitor configuration in response to the sampled pulse amplitude falling to or below a threshold. A request for impedance data may be made after an amplitude threshold crossing during pulse delivery to assist in determining a capacitance required in the second capacitor configuration to adjust the pacing pulse amplitude and maintain it above a minimum amplitude. A new impedance measurement request may additionally or alternatively be made between pacing pulses based on the pulse amplitude reaching an amplitude threshold during the previous pacing pulse.

Microprocessor 140 may determine the initial capacitor configuration by computing the capacitance required to achieve an RC time constant of the capacitor array and known impedance measured for the selected pacing vector that enables maintaining the pulse amplitude above a minimum amplitude for at least the programmed pacing pulse width. Operations performed for determining a capacitor configuration are described below in conjunction with FIGS. 9 through 11.

Timing control module 150 receives pacing pulse timing data from microprocessor 140, including starting time of a scheduled pacing pulse and the pulse width. The time to start pacing pulse delivery and the pulse width are passed to capacitor selection and control module 104. Capacitor selection and control module 104 selects the capacitor configuration according to the configuration data received from capacitor configuration module 146 and couples the selected capacitor configuration to the output signal line 130 according to a pacing pulse start time passed from timing control module 150, e.g., based on the expiration of a pacing escape interval or other inter-pulse interval. Capacitor selection and control module 104 uncouples the selected capacitor configuration from the output signal line 130 upon expiration of the pacing pulse width received from timing control module 150.

Figure 6:
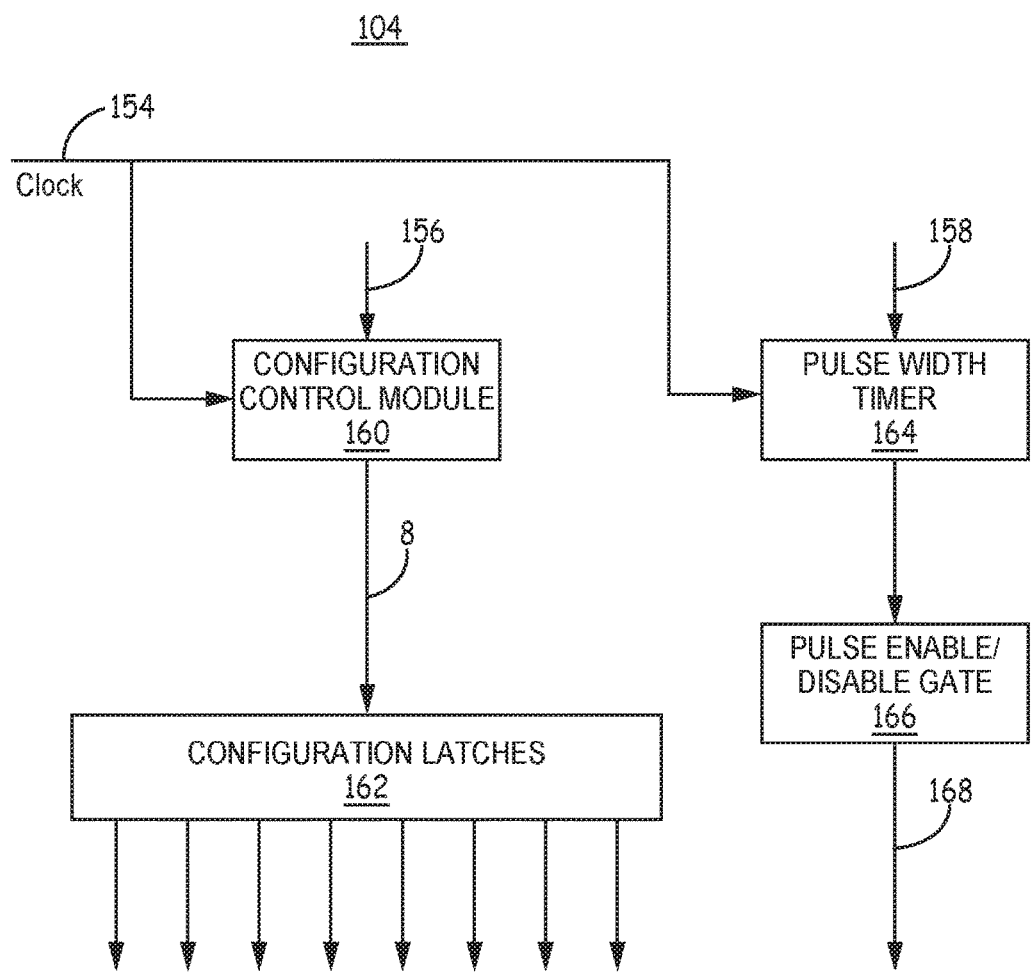
FIG. 6 is a schematic diagram of a capacitor selection and control module included in the therapy delivery module of FIG. 4.

FIG. 6 is a schematic diagram of capacitor selection and control module 104 according to one example. Capacitor selection and control module 104 includes a configuration control module 160, configuration latches 162, a pulse width timer 164 and pacing pulse enable/disable gate 166. Configuration control module 160 receives a clock signal 154 and an input signal 156 from capacitor configuration control module 146 of pacing control module 102 (FIG. 5). The input signal 156 includes capacitor configuration data indicating the number of capacitors C1 through C6 that are to be coupled to output signal line 130 for delivering the next pacing pulse.

Configuration control module 160 clocks the capacitor configuration data stored in buffers or other memory devices to configuration latches 162, which store the configuration data until passed to the S1-S6 switches of the capacitor array 110 (FIG. 4). In accordance with the configuration data, configuration latches 162 set separate signals that are passed to each of the respective switches S1-S6 to selectively enable or disable each one of capacitors C1 through C6 for pacing pulse delivery. Disabled capacitors may be charged and remain charged until needed for pacing pulse delivery but are not coupled to output signal line 130 for pacing pulse delivery. Disabled capacitors may be initially inactive during a pacing pulse, i.e., not coupled to output signal line 130, but are ready to be enabled for pacing pulse delivery if an adjusted capacitor configuration is deemed necessary during the pacing pulse. Disabled capacitors are enabled by being coupled to output signal line 130 via appropriate control of switches S1 through S6.

Configuration control module 160 receives initial capacitor configuration data via input signal 156 that sets the configuration data for selectively enabling or disabling each one of capacitors C1 through C6 according to an initial capacitance requirement to achieve an RC time constant that is longer than the pacing pulse width or other predefined time interval threshold. The configuration data is passed to configuration latches 162 which enable the capacitor(s) included in the initial capacitor configuration to be used for pacing pulse delivery.

Pulse width timer 164 receives clock signal 154 and input from timing control module 150 (FIG. 5) on signal line 158. Pulse width timer passes a timing control signal to pulse enable/disable gate 166. For example, upon expiration of a pacing escape interval, timing control module 150 passes a signal to pulse width timer 164 to enable LV therapy delivery module 85 to start a pacing pulse. Pulse enable/disable signal gate 166 outputs a signal on signal line 168 to switch 112 (FIG. 4) to start the pacing pulse. Switch 112 is controlled by gate 166 to couple the selected capacitor configuration to pacing pulse output signal line 130.

After the initial capacitor configuration is coupled to the pacing pulse output signal line 130 via switch 112, configuration control module 160 may receive new capacitor configuration data via signal line 156 from pacing control module 102 if the sampled pacing pulse amplitude falls to or below an amplitude threshold. As described above, pacing control module 102 receives the sampled pacing pulse output signal amplitude and compares the sampled amplitude to the amplitude threshold. If the pacing pulse amplitude does not fall to or below an amplitude threshold during the pulse width, the initial capacitor configuration remains unchanged during the pacing pulse. If the amplitude falls to or below the amplitude threshold during the pacing pulse width, new capacitor configuration data is passed to configuration control module 160 during the present pacing pulse delivery. Configuration control module 160 passes new configuration data to configuration latches 162 which causes at least one capacitor to be enabled that was not included in the initial capacitor configuration by coupling the capacitor in with the initial capacitor configuration via a respective switch (one of switches S1-S6). Capacitors selected for the initial configuration may be deactivated (switched out of the discharge circuit by uncoupling from output signal line 130) in the adjusted capacitor configuration to prevent charge distribution to those capacitors rather than to the pulse output signal line 130 in some cases. New configuration data may be passed to configuration control module 160 and onto configuration latches 162 multiple times during a given pacing pulse if the sampled pacing pulse amplitude decays to or below an amplitude threshold more than once before the pulse width expires due to the programmed pulse duration exceeding the discharge capacity of the currently selected capacitor configuration.

Upon expiration of the pacing pulse width, pulse width timer 164 passes a pulse termination signal to pulse enable/disable gate 166 that outputs a signal on control signal line 168 that terminates the pacing pulse by disabling switch 112 to uncouple the selected capacitor configuration from output signal line 130. Pacing control module 102 passes capacitor configuration data to configuration control module 160 for the next scheduled pacing pulse. The capacitor configuration for the next scheduled pacing pulse may be re-determined by microprocessor 140 based on a new pacing vector impedance measurement or selected as the final capacitor configuration upon expiration of the preceding pacing pulse. Prior pacing pulse amplitude behavior, which may be influenced by pacing vector impedance variations, may influence the capacitor configuration selected for the next pacing pulse delivery.

Figure 7A:
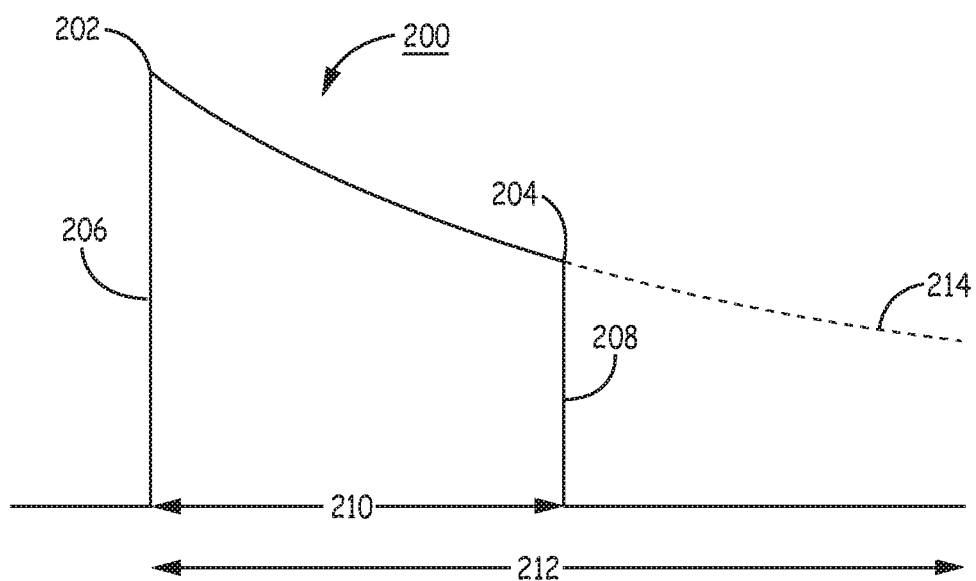
FIG. 7A is a conceptual diagram of a pacing pulse generated by the therapy delivery module of FIG. 4.

FIG. 7A is a conceptual diagram of a pacing pulse 200 generated by LV therapy delivery module 85. Pacing pulse 200 has an initial or leading edge pulse amplitude 202 determined by the charge value of the capacitor configuration, in accordance with the programmed pacing pulse voltage amplitude. The leading edge pulse amplitude may be, for example with no limitation intended, approximately 5 V to 8 V. The pacing pulse leading edge 206 occurs when pulse enable/disable gate 166 enables or closes switch 112 to electrically couple a selected capacitor configuration of capacitor array 110 to output signal line 130. The selected capacitor configuration discharges through the impedance of the pacing electrode vector during the predetermined pacing pulse width 210. Upon expiration of the pacing pulse width 210, the pulse enable/disable gate 166 disables or opens switch 112 to terminate the pacing pulse at terminating edge 208. The pacing pulse has a truncated pulse amplitude 204 at the expiration of the pacing pulse width 210.

The amplitude of the pacing pulse 200 decays from the leading edge amplitude 202 to the truncated amplitude 204 over the pacing pulse width 210 as the selected capacitor configuration discharges through the pacing electrode vector impedance according to an RC time constant 212. The RC time constant 212, sometimes referred to as "tau," is the product of the pacing electrode vector impedance and the capacitance of the selected capacitor configuration. By definition, the RC time constant is the time for a capacitor to discharge through a resistance to approximately 36.8% of its initial charge. A change in pacing vector impedance alters the impedance in the RC time constant, altering the discharge rate of the capacitor configuration, observed as the decay rate of the pacing pulse amplitude. In some examples, the pacing control module 102 is configured to detect a decay rate that is occurring too quickly for the pacing pulse width 210 by comparing sampled pulse amplitude values to a threshold amplitude and responding by adjusting the capacitor configuration to restore a higher pulse amplitude, a slower decay rate or both.

Microprocessor 140 of pacing control module 102 is configured to determine a capacitor configuration including one or more capacitors of capacitor array 110 having an overall capacitance that, with the measured impedance of the pacing electrode vector, results in an RC time constant 212 that is greater than the programmed pacing pulse width 210. In some examples, the capacitor configuration is selected such that the truncated amplitude 204 is expected to be greater than a predetermined percentage of the leading edge amplitude 202, e.g., greater than 50% of the leading edge amplitude 202. A threshold voltage requirement of the truncated amplitude 204 may be defined in order to promote successful capture of the myocardium prior to or upon termination of the pacing pulse 200. When extra-cardiovascular electrodes are used for delivering pacing pulses, the leading edge amplitude 202 may be kept relatively low, e.g., 8 Volts or less and below a pain threshold of the patient. In order to deliver enough energy to successfully capture the myocardium, a relatively long pacing pulse width 210 may be required. If the RC time constant 212 of a selected capacitor configuration is too short, the pacing pulse amplitude may decay too quickly such that the truncated amplitude 204 is below a minimum threshold and the total pacing pulse energy is inadequate to capture and pace the heart.

In order to promote successful capture, the pacing control module 102 may be configured to select the capacitor configuration so that the RC time constant 212 is greater than a time interval threshold. For example, the capacitor configuration may be selected to have a capacitance resulting in an RC time constant 212 that is at least greater than the programmed pacing pulse width 210 or a multiple thereof or greater than a maximum programmable pacing pulse width or a multiple thereof, e.g., twice or three times the maximum programmable pacing pulse width. In one example, the pulse width may be programmable between 1.5 ms and 20 ms. The capacitor configuration is selected based on the measured impedance of the pacing vector so that the resulting RC time constant 212 of the discharge circuit (the selected capacitor configuration discharging through the pacing electrode vector impedance) is longer than the pacing pulse width 210 and the truncated amplitude 204 is greater than an amplitude threshold at the expiration of the pacing pulse 200. By selecting a capacitor configuration having a capacitance that results in an RC time constant meeting these criteria, the voltage amplitude over the duration of the pacing pulse is controlled within an acceptable voltage range and the delivered pulse energy can be expected to successfully pace the heart.

Figure 7B:
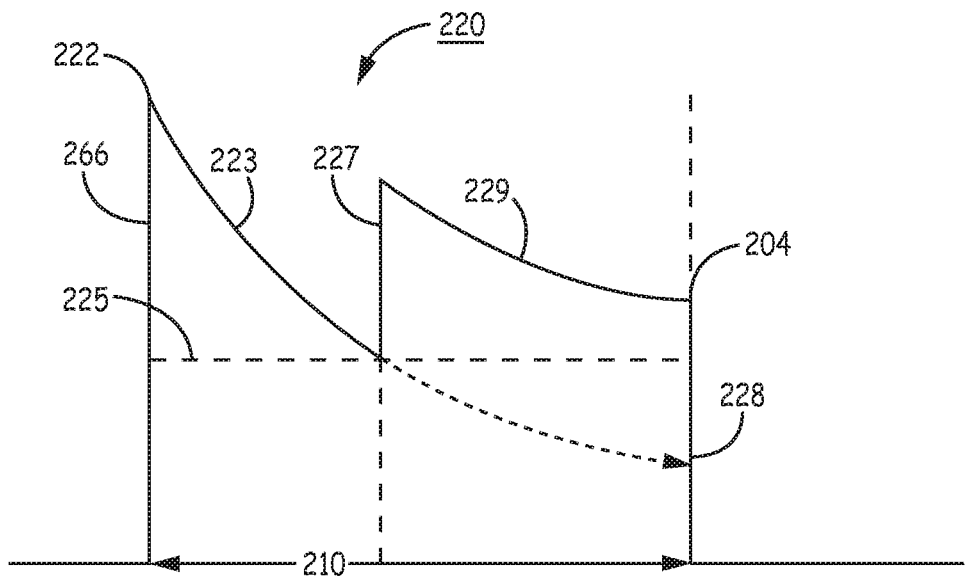
FIG. 7B is a conceptual diagram of a pacing pulse that may be delivered by the IMD of FIG. 1 using a capacitor configuration that is adjusted during the pacing pulse delivery.

FIG. 7B is a conceptual diagram of a pacing pulse 220 that may be delivered by IMD 14 using a capacitor configuration that is adjusted during the pacing pulse delivery. Pacing pulse 220 has an initial or leading edge pulse amplitude 222 determined by the charge value of the capacitor configuration, in accordance with the programmed pacing pulse voltage amplitude. The pacing pulse leading edge 226 occurs when pulse enable/disable gate 166 enables or closes switch 112 to electrically couple a selected capacitor configuration of capacitor array 110 to output signal line 130. The selected capacitor configuration discharges through the impedance of the pacing electrode vector with a decay rate 223 that may be faster than expected causing the pacing pulse amplitude to fall below an amplitude threshold 225 prior to expiration of the programmed pacing pulse width 210.

Pacing control module 102 may monitor the sampled pulse amplitude, and, if the pulse amplitude falls to the threshold 225, pacing control module 102 passes a new capacitor configuration to capacitor selection and control module 104. The adjusted capacitor configuration is enabled at 227. Upon enabling the adjusted capacitor configuration, the pulse amplitude is increased above the threshold 225 and decays at a second decay rate 229 until the pulse width 210 expires. The second decay rate 229 may be the same or different than the first decay rate 223 depending on the relative capacitances of the initial capacitor configuration and the adjusted capacitor configuration. The increase in pulse amplitude achieved by coupling at least one charged capacitor to the discharge circuit during the pacing pulse 220 maintains the pacing pulse amplitude within an acceptable voltage range, e.g., between and including the programmed pulse amplitude (corresponding to leading edge amplitude 222) and the amplitude threshold 225. The adjusted capacitor configuration prevents the pulse amplitude from falling below the amplitude threshold 225. The truncation amplitude 224 is greater than the amplitude threshold 225 at terminating edge 228 of pulse 220.

In some examples, threshold 225 is set greater than a minimum acceptable pulse amplitude threshold so that the capacitor configuration can be adjusted before the pulse amplitude reaches the minimum acceptable threshold. For example, if the programmed pulse amplitude is 5 V, a minimum acceptable threshold may be 2.5 V. The amplitude threshold 225 used for triggering a capacitor configuration adjustment may be 2.75 V so that the pulse amplitude is always maintained above the minimum acceptable threshold.

Extra-cardiovascular leads and pacing electrodes may be subjected to body motion resulting in shifting of the pacing electrodes and changes in the pacing electrode vector impedance. Acute or chronic changes in the impedance of a pacing electrode vector will be accounted for in determining a capacitor configuration for a given measured impedance. In some cases, pacing electrode vector impedance may change during a pacing pulse. When pacing control module 102 is configured to monitor the pulse amplitude in real time, the pacing control module 102 can respond to a change in pacing electrode vector impedance during a pacing pulse by adjusting the capacitor configuration.

Figure 7C:
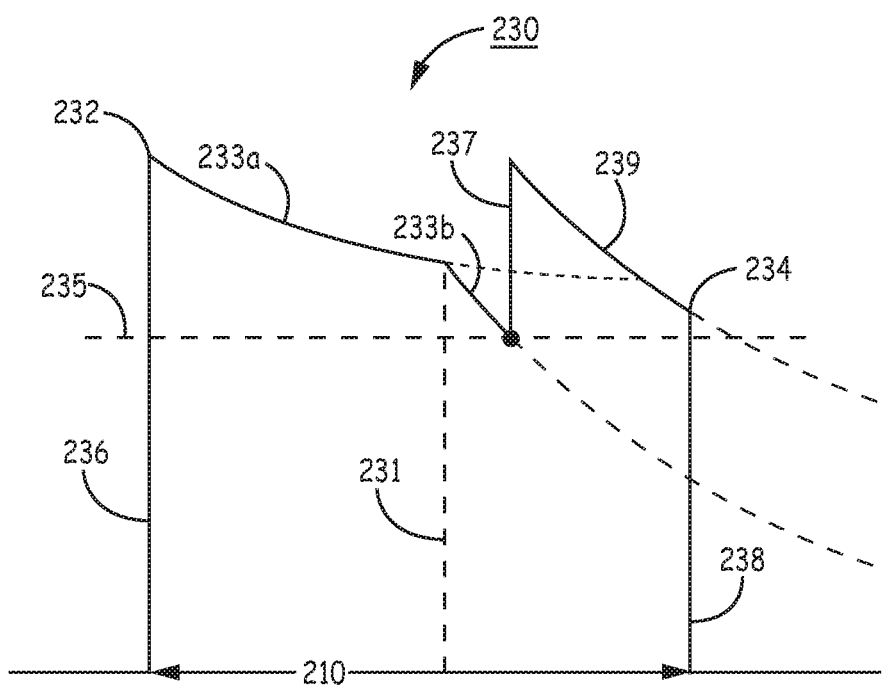
FIG. 7C is a conceptual diagram of one example of a pacing pulse that may be delivered by the IMD of FIG. 1 using an adjusted capacitor configuration during the pacing pulse when a pacing electrode vector impedance change occurs.

FIG. 7C is a conceptual diagram of one example of a pacing pulse 230 that may be delivered by IMD 14 using an adjusted capacitor configuration during the pacing pulse when a pacing electrode vector impedance change occurs. Pacing pulse 230 has a pulse amplitude 232 at the leading edge 236 that is determined by the charge value of the initial capacitor configuration that is selected and based on the programmed pacing pulse amplitude. The pacing pulse decays from the leading edge amplitude 232 at an initial decay rate 233a according to the RC time constant of the discharge circuit. The RC time constant is a function of the capacitance of the initial capacitor configuration and the impedance of the pacing electrode vector. At time 231, during the pacing pulse 230, a change in pacing vector impedance occurs, e.g., due to a shift in electrode location or other factors. A decrease in impedance causes the pulse to decay at a faster decay rate 233b after time 231 in this example. The faster decay rate 233b causes the pulse amplitude to reach amplitude threshold 235 prior to the expiration of pulse width 210.

In this example, pacing control module 102 is configured to monitor the pulse amplitude samples received from ADC 106 in real-time and determine if the pulse amplitude reaches the amplitude threshold 235 during the pacing pulse. As described previously, the threshold 235 may be set as a percentage of programmed pulse amplitude and may define a minimum acceptable voltage amplitude or be greater than the minimum acceptable voltage amplitude so that the pulse amplitude can be adjusted in real time to be maintained within an acceptable voltage range.

Upon detecting that the pulse amplitude has reached the amplitude threshold 235, pacing control module 102 passes adjusted capacitor configuration data to capacitor selection and control module 104. Capacitor selection and control module 104 enables the new capacitor configuration to begin discharging across the pacing vector resulting in a step increase 237 of the pacing pulse amplitude. The step increase 237 is achieved by switching in at least one fully charged capacitor to begin discharging during the pacing pulse 230. Capacitors included in the initial capacitor configuration may be disabled or may remain enabled in the adjusted capacitor configuration.

The pulse 230 decays at a third decay rate 239 after the step increase in amplitude. The third decay rate 239 will depend on the capacitance of the adjusted capacitor configuration and the impedance of the pacing electrode vector. In this example, the capacitance of the adjusted capacitor configuration may be the same as the initial capacitor configuration such that decay rate 239 is approximately the same as the second decay rate 233b after the pacing vector impedance change at 231. The step increase 237 in pulse amplitude, however, maintains the pulse amplitude within an acceptable range such that the truncated amplitude 234 at terminating edge 238 is still greater than the amplitude threshold 235. In other examples, the adjusted capacitor configuration may be selected to have a higher capacitance than the initial capacitor configuration to slow the decay rate 239 after the decrease in pacing electrode vector impedance.

Figure 8:
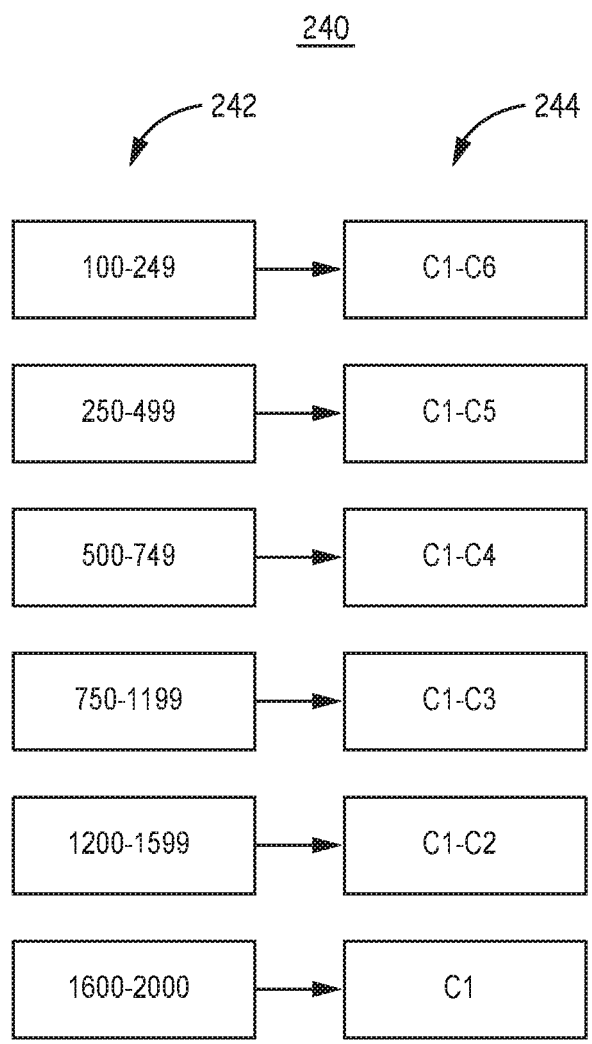
FIG. 8 is a conceptual diagram of a look-up table stored in memory of the IMD of FIG. 1.

FIG. 8 is a conceptual diagram of a look-up table 240 stored in memory 82 accessible by pacing control module 102. Various capacitor configurations may be stored in memory 82, e.g., in the form of a look-up table, for different values of pacing electrode vector impedance. The look-up table 240 includes multiple impedance ranges 242 (listed in ohms), and a capacitor configuration 244 stored for each impedance range. Microprocessor 140 may be configured to fetch an impedance measurement from data buffer 144 (FIG. 5) and compare the impedance measurement to the multiple impedance ranges 242 included in the look-up table 240. When the range of impedance is identified that includes or matches the impedance measurement, the microprocessor 140 selects the capacitor configuration that is stored for the matching impedance range.

As seen in the example of FIG. 8, the capacitor configurations 244 range from a capacitor configuration including all six capacitors, C1-C6, of capacitor array 110 when the measured impedance is between 100 and 249 ohms, inclusive, to a capacitor configuration including only one capacitor, C1, when the measured impedance is between 1600 and 2000 ohms, inclusive.

Using the example of capacitors C1-C6 each being 20 microfarad capacitors, the RC time constant for the first capacitor configuration C1-C6 is approximately 12 ms to 30 ms, depending on the measured impedance in the first range of 100 ohms to 240 ohms. The RC time constant is between approximately 25 ms and 50 ms for the second capacitor configuration C1-C5, between approximately 40 and 75 ms for the C1-C4 configuration, between approximately 45 and 72 ms for the C1-C3 configuration, between approximately 48 and 64 ms for the C1-C2 configuration and between approximately 32 and 40 ms for the C1 configuration. Accordingly, for a pulse width of 10 ms, the RC time constant for a given impedance measurement and its associated capacitor configuration is greater than the 10 ms pulse width for all possible capacitor configurations. If the maximum programmable pulse width is as high as 20 ms, all capacitor configurations have an RC time constant greater than the maximum programmable pulse width with the exception of the case when the pacing vector impedance approaches the minimum listed impedance of 100 ohms.

A pacing vector impedance of 100 ohms is relatively low, but may occur in some instances. For pacing pulse widths of 10 ms or greater, the leading edge pulse amplitude may be required to be relatively higher in order to deliver adequate energy prior to expiration of the pacing pulse. For a shorter pulse width, e.g., 5 ms, the truncated amplitude is 3.29 V when the leading edge amplitude is 5 V and the capacitor configuration C1-C6 is used. The truncated amplitude is greater than 50% of the leading edge amplitude.

In other examples, a stored look-up table such as table 240 is not required. Microprocessor 140 may compute the capacitance required to obtain an RC time constant greater than a threshold time interval for the known, measured impedance. Microprocessor 140 may then select the number of capacitors C1-C6 required to achieve an overall capacitance that is equal to or greater than the computed, required capacitance.

In the example look-up table 240 of FIG. 8, C1 is the default capacitor enabled for all pacing pulses. Capacitors C2 through C6 may be added to a capacitor configuration as needed in a Cn+1 order, e.g., the configuration of C1-C2 may be selected if two capacitors are needed, the configuration C1-C2-C3 may be selected if three capacitors are needed and so on up to C1 through C6 if all capacitors are included in the selected capacitor configuration.

In other examples, when additional capacitors are needed, capacitor selection and control module 104 may cycle through the remaining capacitors from one pacing pulse to the next. For example, C1 may remain the default capacitor but be paired with a different second capacitor for successive pacing pulses when two capacitors are needed, e.g., C1 and C2 for one pacing pulse, then C1 and C3 for the next pacing pulse, then C1 and C4, and so on. In other examples, capacitor selection and control module 104 may cycle the capacitors selected for generating pacing pulses for a given capacitance requirement of the capacitor configuration. For example, if the selected capacitor configuration includes three capacitors, capacitors C1, C2 and C3 may be enabled for delivering one pacing pulse and capacitors C4, C5 and C6 may be used for delivering the next pacing pulse such that the capacitors are charged and enabled for pulse delivery in an alternating manner. It is to be understood that practice of the techniques disclosed herein are not limited to a particular order or sequence of selecting capacitors included in a capacitor configuration. Rather, the capacitors of array 110 may be selected in any combination in order to achieve a required capacitance to achieve a pacing pulse having the programmed pulse width and truncated voltage amplitude that successfully captures the heart with a high degree of confidence. By cycling or alternating between capacitors of array 110 when not all capacitors are required may allow the LV therapy module 104 to maintain charge on capacitors between pacing pulses, particularly when the pacing rate is relatively fast (shorter escape interval), such as during ATP or rate responsive pacing at a higher rate. If capacitors are charged between pulses to maintain a charge, topping off pacing charge can be performed quickly. If more complete charging is needed, cycling between capacitor configurations allows one capacitor configuration to be charged for every other pacing pulse while a different capacitor configuration is delivering the intervening pacing pulses.

Figure 9:
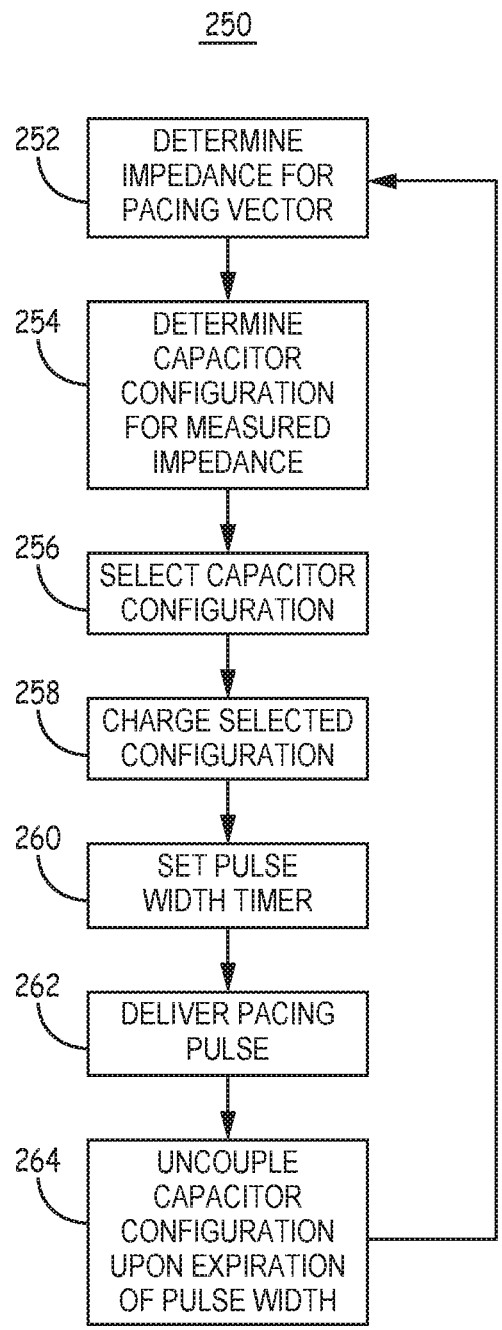
FIG. 9 is a flow chart of a method performed by the IMD of FIG. 1 for delivering a pacing pulse according to one example.

FIG. 9 is a flow chart of a method performed by IMD 14 for delivering a pacing pulse according to one example. At block 252, the control module 80 controls impedance measurement module 90 to measure the impedance of a selected pacing electrode vector, e.g. from electrode 28 to housing 15, from electrode 30 to housing 15, or between electrodes 28 and 30 of FIGS. 1 and 2. At block 254, microprocessor 140 of pacing control module 102 receives the impedance measurement and determines a capacitor configuration for delivering a pacing pulse across the measured impedance of the selected pacing vector for the desired pulse width.

The capacitor configuration may be determined from a look-up table stored in memory 82 as described in conjunction with FIG. 8. Alternatively, the capacitor configuration may be determined by computing the total capacitance required to achieve an RC time constant that is greater than a threshold time interval for the measured impedance of the selected pacing vector. The threshold time interval may be based on the programmed pulse width and/or a minimum amplitude at the terminating pulse edge. The capacitor configuration is then selected at block 256 as the number of capacitors required to meet or exceed the required total capacitance and by identifying the capacitors of capacitor array 110 that are to be enabled in the initial capacitor configuration.

In some examples, the capacitor configuration is determined to achieve an RC time constant that is greater than the delivered pulse width so that the truncated pulse amplitude at the expiration of the delivered pulse width is greater than a minimum threshold. The minimum threshold at the expiration of the pulse width may be a predetermined percentage of the leading edge pulse amplitude, e.g., 50% of the leading edge pulse amplitude.

To illustrate, if the pacing pulse width is programmed to 10 ms, the measured impedance of the pacing electrode vector is 500 ohms, and the capacitor array 110 includes six 20 microfarad capacitors, the capacitor configuration may be determined at block 254 to include three capacitors having a combined capacitance of 60 microfarads. The resulting time constant is 30 ms, greater than the programmed pulse width of 10 ms. If the pacing pulse amplitude is programmed to 5.0 V at the leading edge of the pacing pulse, the truncated voltage amplitude at the expiration of the 10 ms pulse width is expected to be approximately 3.58 V, greater than at least 50% of the leading edge voltage amplitude.

At block 256, the capacitor selection and control module 104 enables the selected capacitor configuration, e.g., by enabling or disabling switches S1 through S6 as required to enable the capacitors selected from C1 through C6 of capacitor array 110. The selected capacitors are charged at block 258 and the pulse width timer 164 is set at block 260. The pacing pulse is delivered at block 262 by enabling switch 112 to couple the selected capacitor configuration to output signal line 130 to allow the capacitor configuration to discharge across the pacing electrode vector. When the pulse width timer 164 expires, switch 112 is disabled or opened to terminate the pacing pulse and uncouple the capacitor configuration from output signal line 130 at block 264.

In flow chart 250, capacitor charging is performed after selection of the individual capacitors of capacitor array 110 for use in the determined capacitor configuration. In some examples, only the capacitors included in the initial capacitor configuration are charged for pacing pulse delivery. In other examples, at least one additional capacitor is charged to be available to be added to the initial capacitor configuration if the pacing pulse amplitude falls to or below a threshold. In still other examples, all capacitors of capacitor array 110 are charged prior to, during or after determination of the capacitor configuration to be used for the next pacing pulse. Only the capacitors selected according to the initial capacitor configuration are coupled to the output signal line 130 for initiating the pacing pulse. Any capacitors not included in the initial capacitor configuration may remain charged and available for selection in a second capacitor configuration selected in response to the pulse amplitude falling below an amplitude threshold prior to pulse width expiration or for selection in an initial capacitor configuration for delivering a future pacing pulse.

After pacing pulse delivery, the process shown in FIG. 9 returns to block 252 to repeat the impedance measurement for the pacing electrode vector. In some examples, the impedance measurement is performed prior to each pacing pulse so that the initial capacitor configuration is set in response to an impedance measurement for each pacing pulse. In other examples, after setting the initial capacitor configuration for the first pulse after an impedance measurement, the same capacitor configuration may be used for subsequent pacing pulses until a capacitor configuration adjustment is required or until another impedance measurement occurs, e.g., on a scheduled basis.

Figure 10:
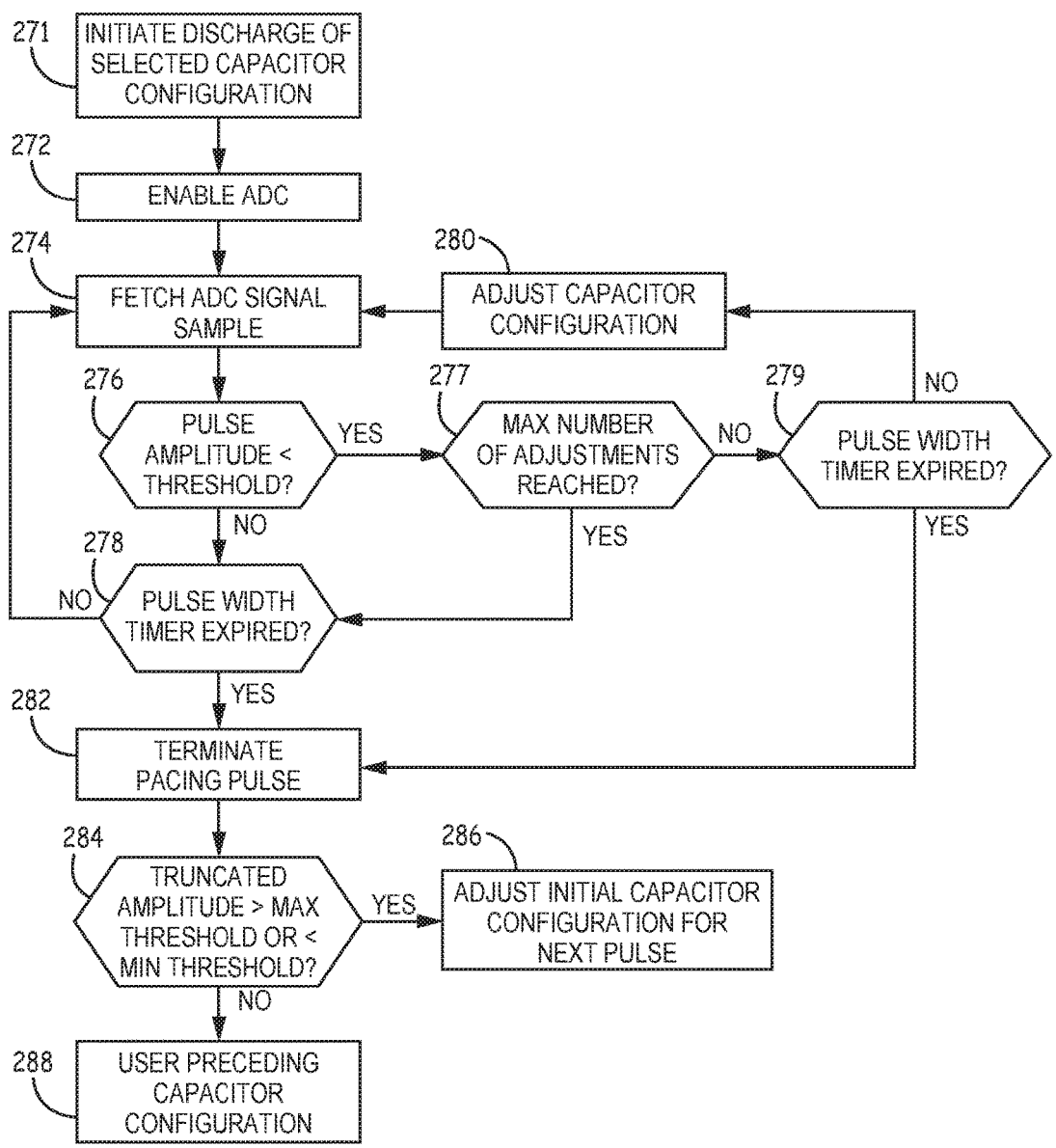
FIG. 10 is a flow chart that corresponds to operations performed in the flow chart of FIG. 9 for delivering a pacing pulse.

FIG. 10 is a flow chart 270 that includes operations that may be performed in block 262 of FIG. 9 for delivering a pacing pulse. Such operations include pacing pulse initiation and termination and amplitude sampling during pulse delivery. The method of flow chart 270 may also include post-pulse delivery assessment of the capacitor configuration used to deliver the pulse to guide selection of the next initial capacitor configuration for delivering the next pacing pulse. At block 271, the pacing pulse is initiated by coupling the selected capacitor configuration to the output signal line 130 at the appropriate time as controlled by pulse width timer 164. The pacing pulse has a leading edge voltage amplitude in accordance with the programmed pulse amplitude.

At block 272, the pacing control module 102 enables the ADC 106 to begin sampling the pacing pulse amplitude at a predetermined sampling rate, e.g., 2 milliseconds. Sampling occurs concurrently with pulse delivery to provide real-time detection of an amplitude threshold crossing. In one example, the ADC 106 is enabled at the leading edge of the pacing pulse and the pacing pulse amplitude is sampled throughout the pacing pulse from the leading edge or the first sampling interval thereafter until the terminating edge or at the last sampling interval preceding the terminating edge. In other examples, the ADC 106 may be enabled to begin sampling after a time delay after the leading edge, e.g. after a portion of the pulse width. For instance, ADC 106 may be enabled to begin sampling half-way through the pacing pulse width and continue sampling the pacing pulse amplitude until the terminating edge or the last sampling interval preceding the terminating edge. In still other examples, the sampling interval may be variable. A longer sampling interval may be used initially and shorten as the terminating edge is approached.

In some cases, the pulse amplitude may be sampled at a mid-point of the pacing pulse width and if the pulse amplitude is at least an expected amplitude or greater, no further sampling is performed during the pacing pulse. Using the example given above, for a 5V pulse having a 10 ms pulse width that is expected to have a truncated amplitude of 3.58 V at 10 ms, if the amplitude is sampled at 5 ms and is at least an expected amplitude based on predictive modeling, e.g., 4.2 V, no further sampling is needed. A reasonable confidence exists that the truncated amplitude will remain above the targeted minimum voltage, e.g., 50% of the leading edge voltage or 2.5 V in this example. If the sampled amplitude is less than an expected midpoint amplitude, however, ADC 106 may be enabled to sample the pacing pulse at a predetermined sampling rate, e.g., every 2 ms or more often, for the remainder of the pacing pulse width.

At block 274 the microprocessor 140 fetches the sampled signal point from data buffer 144 and compares the sampled signal point to an amplitude threshold at block 276. The amplitude threshold used for the comparison at block 276 may be defined as a minimum threshold, e.g., 50% or another percentage of the leading edge amplitude (or programmed pulse amplitude). As suggested above, the amplitude threshold may be a higher threshold used for comparison to sample points acquired earlier in the pacing pulse width. For example, at the midpoint of the pacing pulse width, the sample point may be compared to a higher threshold, e.g., 85% of the programmed pulse amplitude. From the midpoint to the terminating edge of the pulse width, the sampled amplitude may be compared to a lower threshold, e.g., 50% of the programmed pulse amplitude. In other examples, the threshold may be a function of the expired time of the pacing pulse width and based on an expected amplitude according to the RC time constant of the capacitor configuration and measured impedance of the pacing vector.

If the sampled pulse amplitude is less than the amplitude threshold at block 276, the capacitor configuration may be adjusted at block 280. As described above, in some cases, if the pulse amplitude is below a first threshold during a first portion of the pacing pulse width, the ADC 106 may be enabled to sample more frequently during a second portion of the pacing pulse width during which a second lower threshold is used for the comparison at block 276. When the sampled amplitude falls below the second lower threshold, the capacitor configuration adjustment may be made at block 280. In other examples, the capacitor configuration adjustment may be made in response to the sampled amplitude falling to or below the first higher threshold during the first portion of the pacing pulse if detected first and otherwise in response to the sampled amplitude falling to or below the second lower threshold during the second portion of the pacing pulse.

In some examples, a limited number of capacitor configuration adjustments may be performed. For instance, after the capacitor configuration has been adjusted the first time during a pacing pulse at block 280, no further adjustments of the capacitor configuration are made. The ADC 106 may or may not continue to sample the pulse amplitude during the remainder of the pacing pulse after the pacing configuration has been changed. A maximum number of capacitor configuration adjustments greater than one may be allowed, e.g., up to two, three or more adjustments, in which case the ADC 106 continues to sample the pulse amplitude for comparison to the amplitude threshold at block 276 after the first adjustment. If the maximum number of adjustments has been reached as determined at block 277, the process may advance to block 278 to wait for the pulse width timer 164 to expire. If the maximum number of capacitor configuration adjustments has not been reached at block 277, and the pulse width timer has not expired (block 279), the capacitor configuration is adjusted at block 280.

After adjusting the capacitor configuration at block 280, ADC 106 may continue sampling the pacing pulse signal at block 274 and passing signal sample points to data buffer 144 which may store the data on a first-in, first-out basis. If the pacing pulse amplitude falls below a threshold again before the pulse width timer expires, the capacitor configuration may be adjusted again prior to termination of the pacing pulse if the maximum number of adjustments has not been reached.

The ADC 106 may be controlled to sample the pulse amplitude at a regular sampling interval from the onset of the pulse or a predetermined time interval after onset of the pulse until expiration of the pulse width. In other examples, the ADC 106 may be controlled to be disabled prior to completion of the pulse delivery if the pulse amplitude has been sustained at an acceptable level up to a predetermined portion of the pulse width. The time that the ADC 106 is disabled may be based on sampling rate, the programmed pulse width, the expired portion of the pulse width and the pulse amplitude stability during the pulse. "Pulse amplitude stability" refers to the amplitude remaining within a "constant" voltage range as defined for a particular application. The pulse amplitude may decay over the pulse width but remain within a specified "constant" voltage range, e.g., between amplitude threshold and the programmed pulse amplitude. If not, pulse amplitude sampling continues and the capacitor configuration is adjusted as needed. In some examples, all or some of the sample points obtained during the pacing pulse may be passed to memory 82 to be stored for transmission to external device 40 for reviewing and analyzing pacing performance of IMD 14.

If ADC 106 continues to sample the pulse amplitude after the capacitor configuration adjustment while waiting for the pulse width to expire, the additional amplitude data may be used by microprocessor 140 for selecting future initial capacitor configurations for subsequent pacing pulses and/or for selecting adjusted capacitor configurations during subsequent pacing pulses.

Upon expiration of the pulse width timer at block 278, the pacing pulse is terminated at block 282. By adjusting the capacitor configuration during the pacing pulse in response to the pulse amplitude falling to or below an amplitude threshold, the truncated amplitude may be maintained above a minimum threshold amplitude. The truncated amplitude may be sampled to verify that the capacitor configuration adjustment successfully maintained the truncated amplitude above the minimum threshold amplitude. If the truncated pulse amplitude reaches the minimum threshold amplitude at truncation as determined at block 284, microprocessor 140 may adjust the initial capacitor configuration used on a subsequent pacing pulse at block 286 to maintain the pulse amplitude a safety margin above the threshold amplitude at truncation of the next pulse.

In some examples, pacing control module 102 may be configured to adjust an initial capacitor configuration based on the sampled pulse amplitude being greater than an expected maximum threshold. For example, if the truncated amplitude is greater than an expected maximum threshold, as determined at block 284, the capacitance may be higher than necessary for the pacing vector impedance. The initial capacitor configuration may be adjusted for the next pacing pulse by eliminating one capacitor from the configuration at block 286. In some examples, the adjustment of the initial capacitor configuration at block 286 includes repeating an impedance measurement of the pacing vector to re-determine the required capacitance of the capacitor configuration. If the truncated amplitude is less than or equal to an expected maximum threshold and greater than the minimum threshold, the initial capacitor configuration may remain unchanged at block 288 or be set to the final capacitor configuration that was used to deliver the pacing pulse.

Figure 11:
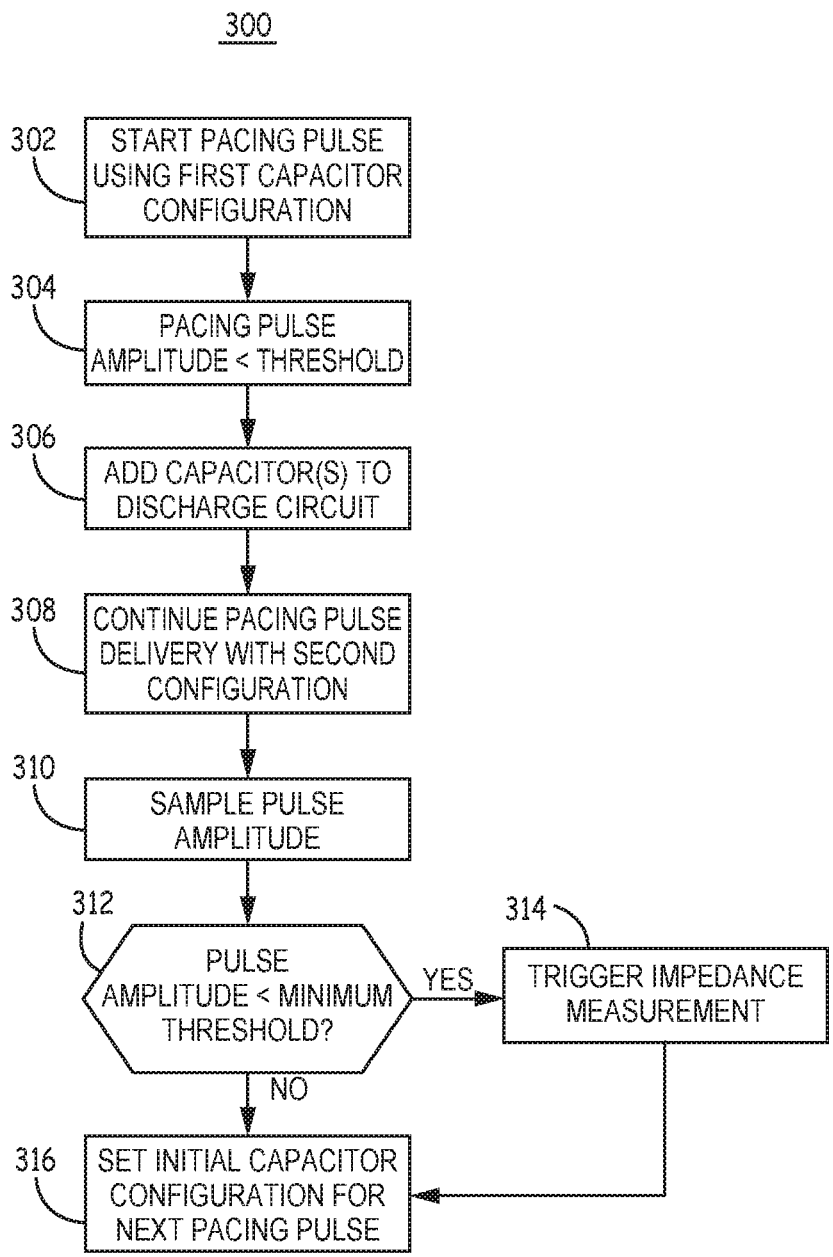
FIG. 11 is a flow chart of a pacing control method according to another example.

FIG. 11 is a flow chart 300 of a pacing control method performed by IMD 14 according to another example. A pacing pulse is started at block 302. The pacing control module 102 starts a pulse width timer and controls the LV therapy delivery module 85 to start discharging an initial capacitor configuration across an extra-cardiovascular pacing electrode vector. The initial capacitor configuration may be a default capacitor configuration, a previously selected capacitor configuration, or set based on a pacing electrode vector impedance measurement.

At block 304, microprocessor 140 determines that the pulse amplitude has fallen to or below an amplitude threshold after a first portion of the pulse width, such that a capacitor configuration adjustment is needed during the pacing pulse. In response to the pulse amplitude falling to or below the amplitude threshold, the pacing control module 102 passes a new capacitor configuration to capacitor selection and control module 104. At block 306, capacitor selection and control module 104 adds one or more capacitors to the initial capacitor configuration according to configuration data received from pacing control module 102 to produce a second capacitor configuration different than the initial capacitor configuration. The second capacitor configuration includes at least one capacitor not included in the initial capacitor configuration but may have been previously charged, e.g., when the initial capacitor configuration was charged. If not previously charged, the capacitor selection and control module 104 enables charging of the one or more capacitors added in the second capacitor configuration and upon charge completion couples the added capacitor(s) to the output signal line by enabling the appropriate switch(es), e.g., one or more of S2 through S6 of FIG. 4 assuming at least C1 is included in the initial capacitor configuration. The capacitors included in the initial capacitor configuration may remain enabled and coupled to output signal line 130 or may be disabled upon adding the one or more capacitors of the second capacitor configuration to the discharge circuit at block 306.

The LV therapy delivery module 85 continues delivering the pacing pulse using the second capacitor configuration at block 308, until the pulse width expires. After enabling the second capacitor configuration, microprocessor 140 may fetch pulse amplitude sample point(s) during a second portion of the pacing pulse for comparison to a minimum threshold at block 310. As long as the sampled pulse amplitude remains greater than the minimum threshold, as determined at block 312, the capacitor configuration adjustment is deemed adequate for maintaining the truncated amplitude of the pacing pulse above a minimum threshold. If the pulse amplitude falls below the minimum threshold at block 312, however, an impedance measurement trigger signal may be generated by microprocessor 140 at block 314. Control module 80 may control impedance measurement module 90 to perform an impedance measurement of the pacing electrode vector prior to the next pacing pulse.

At block 316, pacing control module 102 sets the initial capacitor configuration for the next pacing pulse. If an impedance measurement was triggered at block 314, the pacing control module 102 sets the initial capacitor configuration for the next pacing pulse based on the triggered impedance measurement. The capacitance required to achieve an RC time constant longer than a threshold time interval may be determined using the triggered impedance measurement. The new initial capacitor configuration is selected according to the determined capacitance. Alternatively, the new initial capacitor configuration may be retrieved from a look-up table in memory 82 by matching the measured impedance to a stored impedance range.

If an impedance measurement was not triggered at block 314, the initial capacitor configuration set at block 316 may be set to the same initial capacitor configuration as used on the currently delivered pacing pulse or the adjusted capacitor configuration which was used for delivering the pacing pulse during a second portion of the pulse width. In this way, an impedance measurement may be performed only when triggered in response to the pacing pulse amplitude falling below a minimum threshold after a capacitor configuration adjustment. In various examples, the impedance measurement may be triggered when the capacitor configuration has been adjusted a predetermined number of times, e.g., a single time, two times, or other threshold number of times during a single pacing pulse.

Thus, a method and apparatus for delivering pacing pulses using extra-cardiovascular electrodes have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. An extra-cardiovascular medical device, comprising:
an impedance measurement module configured to measure an impedance of an extra-cardiovascular pacing electrode vector when extra-cardiovascular pacing electrodes are electrically coupled to the medical device;
a therapy delivery module comprising a capacitor array having a plurality of capacitors for producing a pacing pulse; and
a pacing control module coupled to the therapy delivery module and the impedance measurement module and configured to:
control the impedance measurement module to measure the impedance of the extra-cardiovascular pacing electrode vector;
determine a first capacitor configuration based on the measured impedance by determining a capacitance required for the measured impedance to produce an RC time constant that is greater than a time interval threshold and identifying the first capacitor configuration so that the first capacitance is equal to or greater than the determined capacitance, the first capacitor configuration comprising a first combination of the plurality of capacitors having a first capacitance;
control the therapy delivery module to select the first capacitor configuration by selectively enabling the first combination of the plurality of capacitors of the capacitor array; and
control the therapy delivery module to deliver a cardiac pacing pulse by discharging the first capacitor configuration for a predetermined pulse width across the extra-cardiovascular pacing electrode vector.

2. The device of claim 1, wherein the time interval threshold is greater than the pacing pulse width.

3. The device of claim 1, wherein:
the therapy delivery module is configured to sample the amplitude of the pacing pulse during a first portion of the pulse width and during a second portion of the pulse width after the first portion; and
the pacing control module is further configured to:
receive the sampled pacing pulse amplitude from the therapy delivery module;
compare the sampled pacing pulse amplitude to a first threshold during the first portion of the pulse width;
in response to the sampled pacing pulse amplitude being greater than the first threshold, continue delivering the pacing pulse using the first capacitor configuration;
compare the sampled pacing pulse amplitude to a second threshold during the second portion of the pulse width, the second threshold lower than the first threshold;
determine a second capacitor configuration in response to the pacing pulse amplitude being less than or equal to the second threshold during the second portion of the pulse width, the second capacitor configuration comprising a second combination of the plurality of capacitors of the capacitor array;
control the therapy delivery module to select the second capacitor configuration by selectively enabling the second combination of the plurality of capacitors of the capacitor array; and
control the therapy delivery module to continue delivering the pacing pulse by discharging the second capacitor configuration during the second portion of the pulse width.

4. The device of claim 1, wherein:
the therapy delivery module is configured to sample the amplitude of the pacing pulse; and
the pacing control module is further configured to:
receive the sampled pacing pulse amplitude from the therapy delivery module;
compare the sampled pacing pulse amplitude to an amplitude threshold;
in response to the sampled pacing pulse amplitude being greater than the amplitude threshold, adjust the first capacitor configuration to a second combination of the plurality of capacitors of the capacitor array, the second combination having a second capacitance less than the first capacitance;
control the therapy delivery module to enable the adjusted first capacitor configuration by selectively enabling the second combination of the plurality of capacitors of the capacitor array; and
control the therapy delivery module to deliver a next pacing pulse by discharging the adjusted first capacitor configuration for the predetermined pulse width.

5. The device of claim 1, further comprising a memory storing a plurality of impedance ranges and a plurality of capacitor configurations, wherein one of the plurality of capacitor configurations is stored for each one of the plurality of impedance ranges,
wherein the pacing control module is configured to determine the first capacitor configuration by matching the measured impedance to one of the plurality of impedance ranges and selecting the capacitor configuration stored for the matching impedance range.

6. An extra-cardiovascular medical device comprising:
an impedance measurement module configured to measure an impedance of an extra-cardiovascular pacing electrode vector when extra-cardiovascular pacing electrodes are electrically coupled to the medical device;
a therapy delivery module comprising a capacitor array having a plurality of capacitors for producing a pacing pulse; and
a pacing control module coupled to the therapy delivery module and the impedance measurement module and configured to:

control the impedance measurement module to measure the impedance of the extra-cardiovascular pacing electrode vector;

determine a first capacitor configuration based on the measured impedance, the first capacitor configuration comprising a first combination of the plurality of capacitors having a first capacitance;

control the therapy delivery module to select the first capacitor configuration by selectively enabling the first combination of the plurality of capacitors of the capacitor array; and control the therapy delivery module to deliver a cardiac pacing pulse by discharging the first capacitor configuration for a predetermined pulse width across the extra-cardiovascular pacing electrode vector, wherein the therapy delivery module is configured to sample the amplitude of the pacing pulse after a first portion of the pulse width; and the pacing control module is further configured to:

receive the sampled pacing pulse amplitude from the therapy delivery module;

compare the sampled pacing pulse amplitude to a first amplitude threshold;

determine a second capacitor configuration in response to the sampled pacing pulse amplitude being less than or equal to the first amplitude threshold;

control the therapy delivery module to select the second capacitor configuration by selectively enabling the second combination of the plurality of capacitors of the capacitor array; and control the therapy delivery module to continue delivering the pacing pulse by discharging the second capacitor configuration during a second portion of the pulse width, the second portion after the first portion.

7. The device of claim 6, wherein the second capacitor configuration is selected to have a second capacitance that is greater than the first capacitance.

8. The device of claim 6, wherein the pacing control module is configured to set the first amplitude threshold to a percentage of a leading edge amplitude of the pacing pulse.

9. The device of claim 6, wherein the second capacitor configuration comprises the first capacitor configuration and at least one capacitor of the plurality of capacitors that was not included in the first capacitor configuration.

10. The device of claim 6, wherein:

the therapy delivery module is configured to sample the amplitude of the pacing pulse during the second portion of the pulse width; and the pacing control module is further configured to:

compare the amplitude of the pacing pulse during the second portion of the pulse width to a second amplitude threshold; and control the impedance measurement module to repeat the measurement of the impedance of the pacing electrode vector in response to the amplitude of the pacing pulse being less than the second amplitude threshold during the second portion of the pulse width.

11. A method performed by an extra-cardiovascular medical device, comprising:

measuring an impedance of an extra-cardiovascular pacing electrode vector when extra-cardiovascular pacing electrodes are electrically coupled to the medical device;

determining by a pacing control module of the medical device a first capacitor configuration based on the measured impedance by determining a capacitance required for the measured impedance to produce an RC time constant that is greater than a time interval threshold and identifying the first capacitor configuration so that the first capacitance is equal to or greater than the determined capacitance, the first capacitor configuration comprising a first combination of a plurality of capacitors of a capacitor array;

selecting the first capacitor configuration by selectively enabling the first combination of the plurality of capacitors; and delivering a cardiac pacing pulse by discharging the first capacitor configuration for a predetermined pulse width across the extra-cardiovascular pacing electrode vector.

12. The method of claim 11, wherein the time interval threshold is greater than the pacing pulse width.

13. The method of claim 11, further comprising sampling the amplitude of the pacing pulse during a first portion of the pulse width and during a second portion of the pulse width after the first portion;

receiving the sampled pacing pulse amplitude from the therapy delivery module;

comparing the sampled pacing pulse amplitude to a first threshold during the first portion of the pulse width;

in response to the sampled pacing pulse amplitude being greater than the first threshold, continuing delivering the pacing pulse using the first capacitor configuration;

comparing the sampled pacing pulse amplitude to a second threshold during the second portion of the pulse width, the second threshold lower than the first threshold;

determining a second capacitor configuration in response to the pacing pulse amplitude being less than or equal to the second threshold during the second portion of the pulse width, the second capacitor configuration comprising a second combination of the plurality of capacitors of the capacitor array and having a second capacitance greater than the first capacitance;

selecting the second capacitor configuration by selectively enabling the second combination of the plurality of capacitors of the capacitor array; and continuing delivering the pacing pulse by discharging the second capacitor configuration during the second portion of the pulse width.

14. The method of claim 11, further comprising:

sampling the amplitude of the pacing pulse;

comparing the sampled pacing pulse amplitude to an amplitude threshold;

in response to the sampled pacing pulse amplitude being greater than the amplitude threshold, adjusting the first capacitor configuration to a second combination of the plurality of capacitors of the capacitor array, the second combination having a second capacitance less than the first capacitance;

enabling the adjusted first capacitor configuration by selectively enabling the second combination of the plurality of capacitors of the capacitor array; and delivering a next pacing pulse by discharging the adjusted first capacitor configuration for the predetermined pulse width.

15. The method of claim 11, further comprising:

storing in a memory of the medical device a plurality of impedance ranges and a plurality of capacitor configurations, wherein one of the plurality of capacitor configurations is stored for each one of the plurality of impedance ranges; and determining the first capacitor configuration by matching the measured impedance to one of the plurality of impedance ranges and selecting the capacitor configuration stored for the matching impedance range.

16. A method comprising:

measuring an impedance of an extra-cardiovascular pacing electrode vector when extra-cardiovascular pacing electrodes are electrically coupled to the medical device;

determining by a pacing control module of the medical device a first capacitor configuration based on the measured impedance by determining a capacitance required for the measured impedance to produce an RC time constant that is greater than a time interval threshold and identifying the first capacitor configuration so that the first capacitance is equal to or greater than the determined capacitance, the first capacitor configuration comprising a first combination of a plurality of capacitors of a capacitor array;

selecting the first capacitor configuration by selectively enabling the first combination of the plurality of capacitors; and delivering a cardiac pacing pulse by discharging the first capacitor configuration for a predetermined pulse width across the extra-cardiovascular pacing electrode vector;

sampling the amplitude of the pacing pulse after a first portion of the pulse width;

comparing the sampled pacing pulse amplitude to a first amplitude threshold;

determining a second capacitor configuration in response to the sampled pacing pulse amplitude being less than or equal to the first amplitude threshold;

selecting the second capacitor configuration by selectively enabling the second combination of the plurality of capacitors of the capacitor array; and continuing delivering the pacing pulse by discharging the second capacitor configuration during a second portion of the pulse width, the second portion after the first portion.

17. The method of claim 16, wherein determining the second capacitor configuration comprises determining a second capacitance of the second capacitor configuration that is greater than the first capacitance of the first capacitor configuration.

18. The method of claim 16, further comprising setting the first amplitude threshold to a percentage of a leading edge amplitude of the pacing pulse.

19. The method of claim 16, further comprising selecting the second capacitor configuration by selecting the first capacitor configuration and at least one capacitor of the plurality of capacitors that was not included in the first capacitor configuration.

20. The method of claim 16, further comprising:

sampling the amplitude of the pacing pulse during the second portion of the pulse width;

comparing the amplitude of the pacing pulse during the second portion of the pulse width to a second amplitude threshold; and repeating the impedance measurement of the pacing electrode vector in response to the amplitude of the pacing pulse being less than the second amplitude threshold during the second portion of the pulse width.

* * * * *